(12) United States Patent
Gono et al.

(10) Patent No.: US 9,179,829 B2
(45) Date of Patent: Nov. 10, 2015

(54) ENDOSCOPE

(75) Inventors: Takaaki Gono, Hachioji (JP); Naruto Shinkai, Kawasaki (JP); Junichi Adachi, Hachioji (JP); Satoshi Takekoshi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 13/456,359

(22) Filed: Apr. 26, 2012

(65) Prior Publication Data

US 2012/0271103 A1     Oct. 25, 2012

Related U.S. Application Data

(63) Continuation of application No. PCT/JP2011/073069, filed on Oct. 6, 2011.

(30) Foreign Application Priority Data

Oct. 26, 2010   (JP) .................... 2010-240017

(51) Int. Cl.
| | |
|---|---|
| *A61B 1/06* | (2006.01) |
| *A61B 1/00* | (2006.01) |
| *A61B 1/05* | (2006.01) |
| *A61B 1/07* | (2006.01) |

(Continued)

(52) U.S. Cl.
CPC ............ *A61B 1/0638* (2013.01); *A61B 1/00163* (2013.01); *A61B 1/05* (2013.01); *A61B 1/0676* (2013.01); *A61B 1/0684* (2013.01); *A61B 1/07* (2013.01)

(58) Field of Classification Search
CPC ... A61B 1/0646; A61B 1/0684; A61B 1/0638
USPC .......... 600/103, 108–114; 359/350, 462, 798; 385/115–119; 362/551–555
See application file for complete search history.

(56) References Cited

U.S. PATENT DOCUMENTS

| | | | |
|---|---|---|---|
| 7,724,378 | B2 | 5/2010 | Babayoff |
| 2002/0021355 | A1 | 2/2002 | Utsui et al. |

(Continued)

FOREIGN PATENT DOCUMENTS

| | | |
|---|---|---|
| CN | 101248384 A | 8/2008 |
| EP | 1 894 510 A1 | 3/2008 |

(Continued)

OTHER PUBLICATIONS

Extended Supplementary European Search Report dated Mar. 7, 2014 from related European Application No. 11 83 6000.7.

*Primary Examiner* — Anhtuan T Nguyen
*Assistant Examiner* — Rajaa El Alami
(74) *Attorney, Agent, or Firm* — Scully, Scott, Murphy & Presser, PC

(57) ABSTRACT

An endoscope includes: an insertion portion to be inserted into a subject; an operation section provided at a proximal end of the insertion portion; a first light source section provided inside the operation section, the first light source section generating first light as broadband light having a broadband wavelength characteristic; a light guiding section that guides the first light emitted from the first light source section; a second light source section provided on a distal end side of the insertion portion, the second light source section generating second light; and an optical element provided on the distal end side of the insertion portion, the optical element combining the first light and the second light and emitting the resulting light from an illuminating window.

22 Claims, 18 Drawing Sheets

(56) References Cited

U.S. PATENT DOCUMENTS

| | | |
|---|---|---|
| 2003/0120129 A1 | 6/2003 | Nakamura |
| 2010/0118276 A1* | 5/2010 | Li ................... 353/33 |
| 2010/0137682 A1 | 6/2010 | Doguchi et al. |
| 2010/0280322 A1* | 11/2010 | Mizuyoshi ............ 600/178 |

FOREIGN PATENT DOCUMENTS

| | | |
|---|---|---|
| EP | 2 130 484 A1 | 12/2009 |
| JP | 60-076714 | 5/1985 |
| JP | 2002-219102 | 8/2002 |
| JP | 2003-079571 | 3/2003 |
| JP | 2003-164417 | 6/2003 |
| JP | 2003-190091 | 7/2003 |
| JP | 2004-065728 | 3/2004 |
| JP | 2006-136453 | 6/2006 |
| JP | 2006-346358 | 12/2006 |
| JP | 2007-229262 | 9/2007 |
| JP | 2009-297290 | 12/2009 |

\* cited by examiner (A)

(B)

(C)

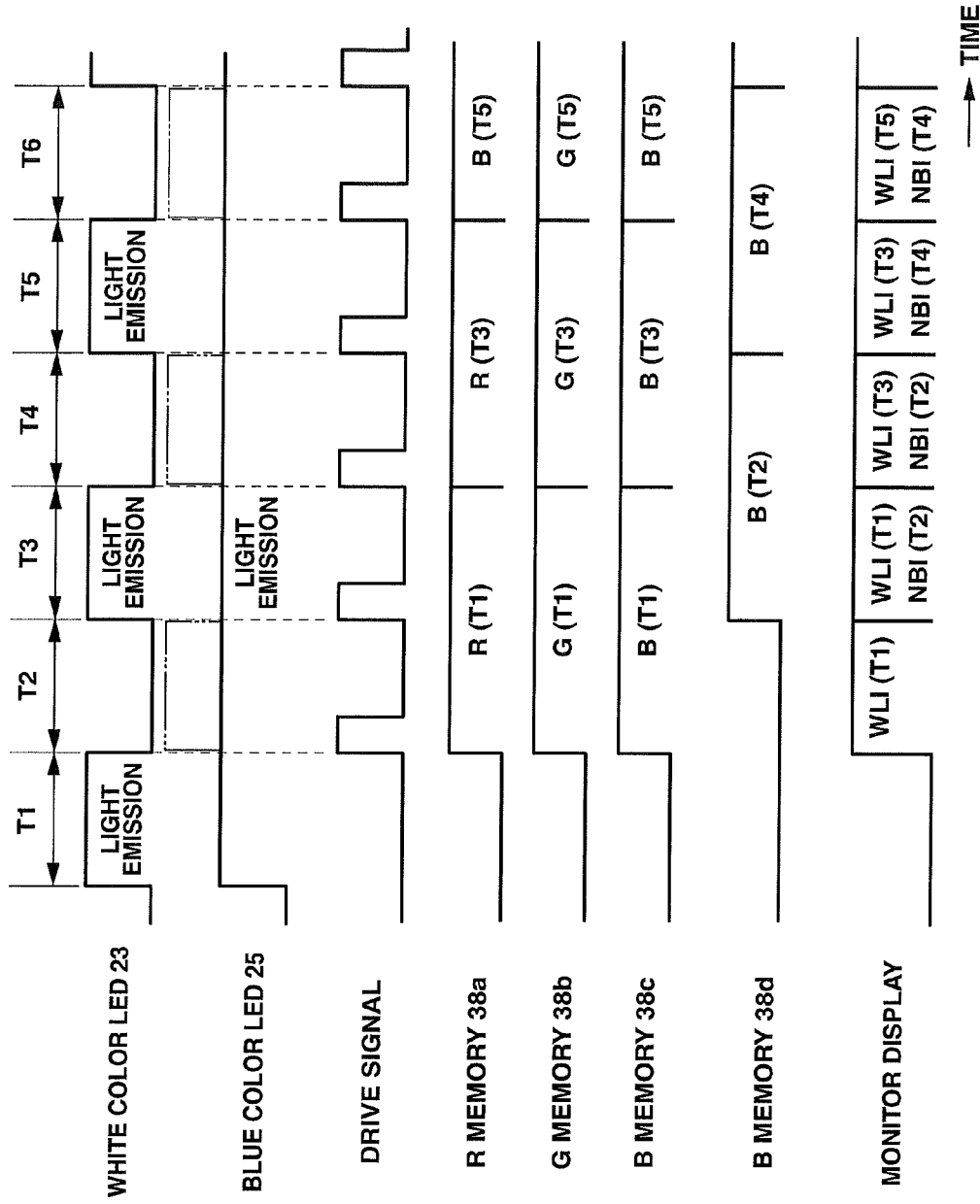

ENDOSCOPE

CROSS REFERENCE TO RELATED APPLICATION

This application is a continuation application of PCT/JP2011/073069 filed on Oct. 6, 2011 and claims benefit of Japanese Application No. 2010-240017 filed in Japan on Oct. 26, 2010, the entire contents of which are incorporated herein by this reference.

BACKGROUND OF THE INVENTION

1. Field of the Invention

The present invention relates to an endoscope that uses broadband light and narrow band light for illuminating light.

2. Description of the Related Art

In recent years, endoscopes have been widely used for endoscopy by inserting an insertion portion into a subject.

An inside of the subject is illuminated with broadband illuminating light covering a visible wavelength band, enabling acquisition of an observed image almost equivalent to observation with bare eyes.

Meanwhile, there are proposed endoscopes that illuminate a site to be observed using narrow band illuminating light covering a certain wavelength band only, in addition to broadband illuminating light covering a visible wavelength band, to acquire an observed image (observed image of flow in vessels near a superficial layer) using narrow band light, which is different from a normal observed image, in order to enhance an imaging function of the endoscopes.

For example, a first related art endoscope disclosed in Japanese Patent Application Laid-Open Publication No. 2003-079571 includes a first light-emitting device in a distal end portion of an insertion portion, and light emitted from the first light-emitting device is emitted to the inside of a living body via a first light distribution lens.

Furthermore, it is disclosed that a second light-emitting device is provided in an operation section, and light emitted from the second light-emitting device is guided by a light guide and emitted from a distal end face of the light guide to the inside of a living body via a second light distribution lens.

Furthermore, an endoscope according to a second related art example disclosed in Japanese Patent Application Laid-Open Publication No. 2003-164417 includes a prism, and the prism guides white color light from a white color light source apparatus or ultraviolet light from an excitation light source to a rear end of a light guide provided through an almost entire length of the inside of the endoscope by, e.g., switching between the white color light and the ultraviolet light, and the guided light is emitted from a distal end face of the light guide via a light distribution lens.

SUMMARY OF THE INVENTION

An endoscope according to an aspect of the present invention includes: an insertion portion to be inserted into a subject; an operation section provided at a proximal end of the insertion portion, the operation section including operation means; a first light source section provided inside the operation section, the first light source section generating first light having a wavelength characteristic including a visible wavelength band; a light guiding section including an entrance portion provided on a proximal end side of the insertion portion and an emitting portion provided on a distal end side of the insertion portion, the light guiding section guiding the first light entering the entrance portion and emitting the first light from the emitting portion; a second light source section that generates light in a wavelength band in which attenuation occurs when the first light is guided by the light guiding section, as second light; and an optical element that combines light emitted from the emitting portion of the light guiding section and the second light and emits the resulting light from an illuminating window.

BRIEF DESCRIPTION OF THE DRAWINGS

FIG. 13C is a diagram illustrating an operation of the sixth variation.

DETAILED DESCRIPTION OF THE PREFERRED EMBODIMENTS

Hereinafter, embodiments of the present invention will be described with reference to the drawings.

First Embodiment

Figure 1:
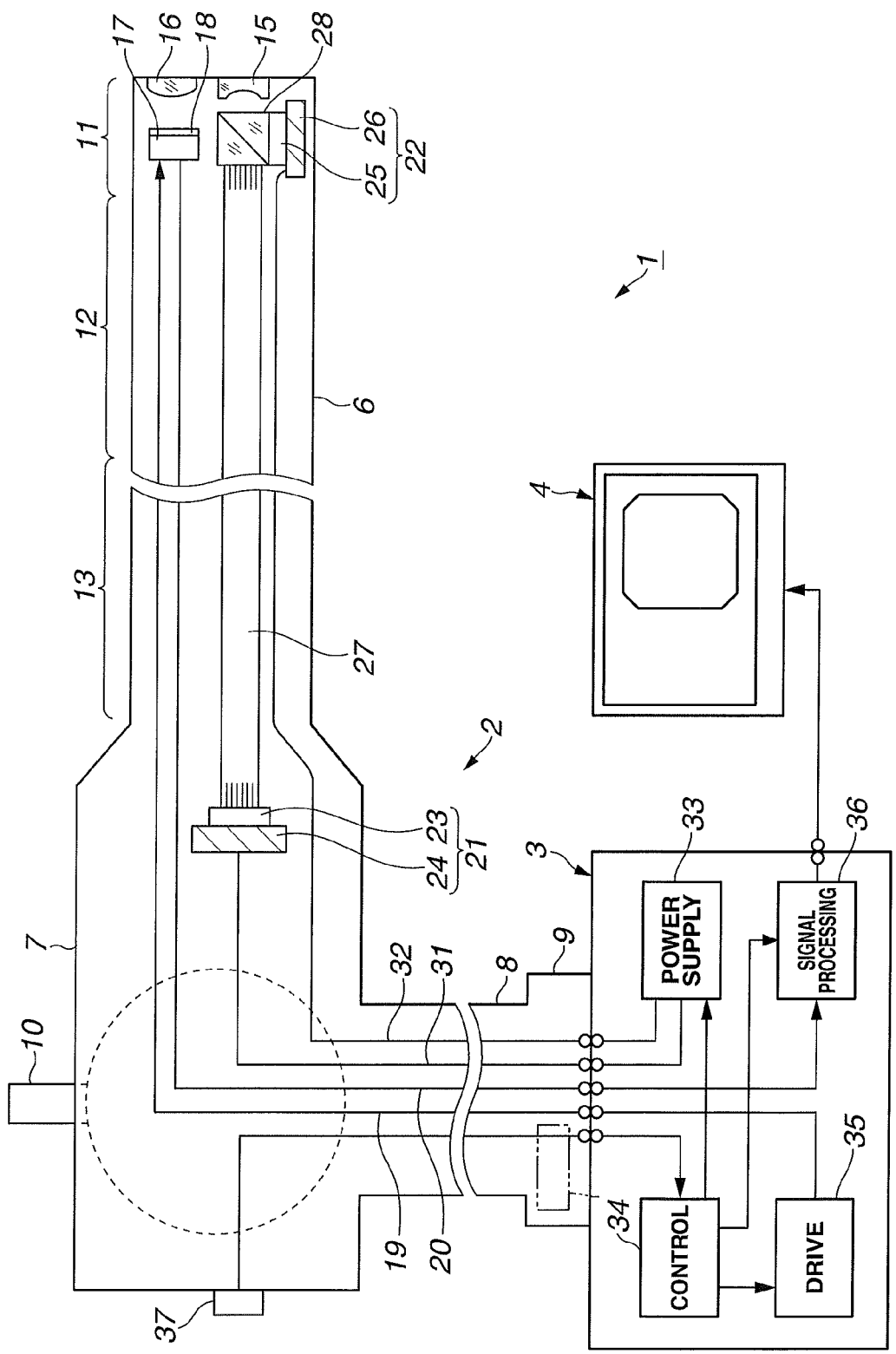
FIG. 1 is an overall configuration of an endoscope apparatus including a first embodiment of the present invention.

As illustrated in FIG. 1, an endoscope apparatus 1 including a first embodiment of the present invention includes an endoscope 2 according to the first embodiment, a video processor 3 as a signal processing apparatus detachably connected to the endoscope 2, and a monitor 4 as display means for, upon input of a video signal from the video processor 3, displaying an endoscopic image corresponding to the video signal.

The endoscope 2 includes an elongated insertion portion 6 to be inserted into a body cavity, an operation section 7 provided at a rear end of the insertion portion 6, the operation section 7 being provided with a bending operation knob 10 as operating means for bending, and a cable 8 extending from the operation section 7. A connector 9 at a terminal of the cable 8 is detachably connected to the video processor 3.

The insertion portion 6 includes a distal end portion 11 provided at a distal end thereof, a bending portion 12 provided at a rear end of the distal end portion 11, and a flexible portion 13 having flexibility and extending from a rear end of the bending portion 12 to a front end of the operation section 7. A surgeon grasps a grasping portion on the front end side of the operation section 7 and performs an operation to rotate the bending operation knob 10, which is operation means for bending, to pull a non-illustrated bending wire, enabling the bending portion 12 to be bent. The bending portion 12 includes a plurality of non-illustrated bending pieces pivotably connected to one another.

At the distal end portion 11 of the insertion portion 6, an illuminating window and an observation window are provided adjacent to each other, and an illumination lens 15 from which illuminating light is emitted to the object side is attached to the illuminating window, and an objective lens 16 that forms an optical image of an illuminated object is attached to the observation window.

A large amount of light in a blue color narrow band on the short wavelength side of the visible wavelength band is lost when the blue color narrow band light is guided by a light guide, which is light guiding means (light conveying means) (in other words, a light guide exhibits a low efficiency for guiding or conveying blue color narrow band light). Accordingly, the present embodiment is configured so that a second light source section 22 that generates the blue color narrow band light is disposed inside the distal end portion 11 as described below. Furthermore, the blue color narrow band light has a small (narrow) wavelength band, and thus, is largely affected by the light amount loss compared to a case of broadband light.

Meanwhile, a first light source section 21 that generates white color light as broadband light covering a visible wavelength band is disposed at the operation section 7. The broadband light suffers only a small (low) effect of light amount loss when the broadband light is guided by the light guide compared to the case of the blue color narrow band light. The light is guided to the distal end portion 11 side by the light guide 27.

In other words, the endoscope 2 in the present embodiment includes the first light source section 21 that generates white color light as broadband light covering a visible wavelength band inside the operation section 7, and the second light source section 22 that generates light in a blue color narrow band on the short wavelength side of the visible wavelength band.

The first light source section 21 includes a white color light-emitting diode (abbreviated as "LED") 23 that generates white color light as broadband light, and an LED substrate 24 with the white color LED 23 mounted thereon.

Meanwhile, the second light source section 22 includes a blue color LED 25 that generates blue light as narrow band light, and an LED substrate 26 with the blue color LED 25 mounted thereon.

On an emission face of the white color LED 23 from which white color light is emitted, a rear end face (proximal end face) of the light guide fiber (simply abbreviated as "light guide") 27, which is included in a light guiding section, is disposed so as to be in contact with the emission face, and the light guide 27 guides (conveys) entered white color light and emits the white color light from a distal end face (emission face) of the light guide 27.

Figure 2:
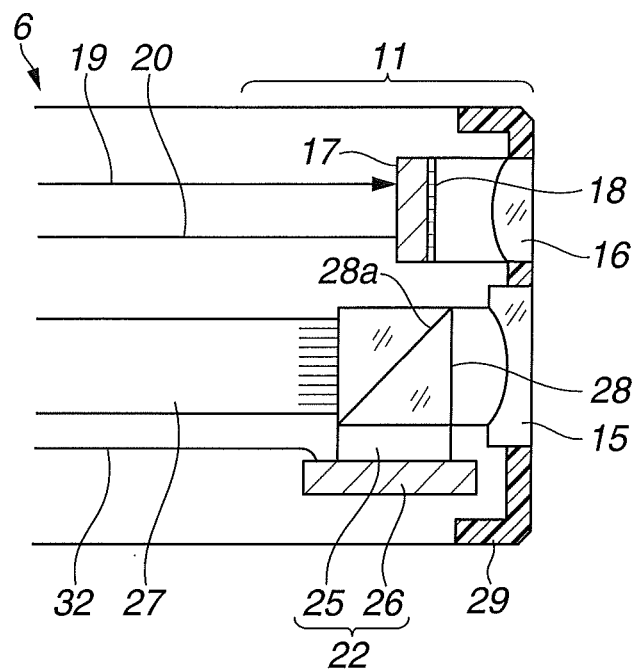
FIG. 2 is an enlarged diagram illustrating a configuration of a distal end portion in FIG. 1.

As illustrated in FIGS. 1 and 2, the distal end face of the light guide 27 is fixed inside the distal end portion 11 in such a manner that the distal end face is in contact with a face of a prism 28 opposed to an emission face thereof (referred to as a first entrance face), the prism 28 including a face opposed to the illumination lens 15 attached to an opening of the illuminating window inside the distal end portion 11, as the emission face.

Also, a second entrance face of the prism 28 perpendicular to the first entrance face is fixed inside the distal end portion 11 in such a manner that an emission face of the blue color LED 25 is in contact with the second entrance face.

Furthermore, the LED substrates 24 and 26 are connected to a power supply circuit 33 inside the video processor 3 to which the connector 9 is connected, via power supply wires 31 and 32 inserted in the endoscope 2, respectively.

Then, drive voltage from the power supply circuit 33 is supplied to the LED substrates 24 and 26, enabling driving of the white color LED 23 and the blue color LED 25 to emit light. The power supply circuit 33 operates under the control of the control circuit 34. Here, although in FIG. 1, the control circuit 34 is provided inside the processor 3, the control circuit 34 may be provided inside the endoscope 2. For example, as shown by the alternate long and two short dashes lines, the control circuit 34 may be provided inside the connector 9.

Figure 3:
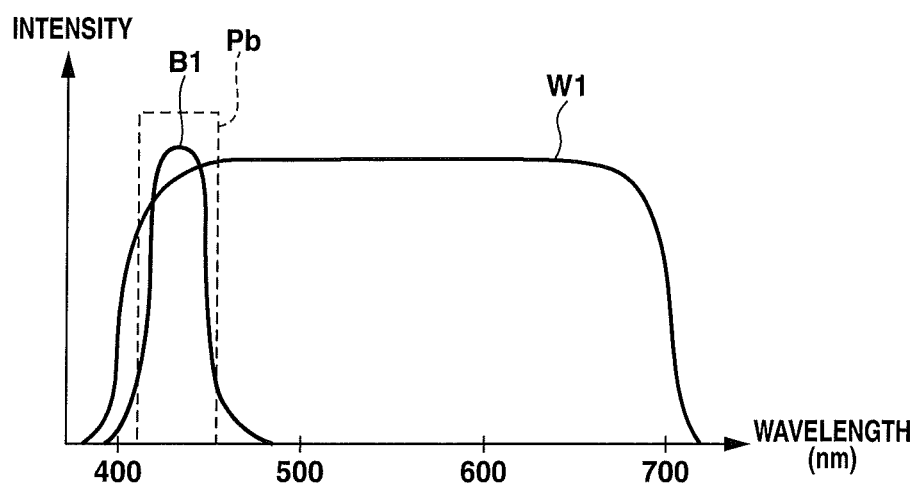
FIG. 3 is a diagram illustrating a wavelength band of broadband light and a wavelength band of narrow band light generated by a first light source section and a second light source section, respectively.

Once the drive power is fed from the power supply circuit 33, the white color LED 23 and the blue color LED 25 generate white color broadband light covering a visible wavelength band (indicated by W1 in FIG. 3) and light in a blue color narrow band on the short wavelength side of the visible wavelength band (indicated by B1 in FIG. 3), respectively, as illustrated in, for example, FIG. 3.

The prism 28 includes a dichroic prism set to have a characteristic of selectively reflecting, for example, (light in a wavelength band that is the same as that of) the blue color narrow band light illustrated in FIG. 3, and selectively transmitting white color broadband light other than the blue color narrow band light.

More specifically, a dielectric film 28a set to have a characteristic Pb of selectively reflecting the blue color narrow band light, which is indicated by the dotted line in FIG. 3, is formed on inclined joining surfaces of the two triangular prisms included in the prism 28.

Accordingly, the white color broadband light generated by the white color LED 23 is guided by the light guide 27, and the white color broadband light other than the blue color narrow band light penetrates the prism 28, and is emitted via the illumination lens 15 attached to the illuminating window and illuminates the object side such as a diseased part. Meanwhile, the blue color narrow band light generated by the blue color LED 25 disposed inside the distal end portion 11 is reflected by the prism 28 and is emitted via the illumination lens 15 attached to the illuminating window and illuminates the object side such as a diseased part.

Also, as illustrated in FIG. 2, on the distal end face side of the distal end portion 11, a distal end cover 29 having elasticity is provided.

Also, at an image forming position of the objective lens 16, an image pickup surface of, for example, a charge-coupled device (abbreviated as CCD) 17, which is an image pickup device, is disposed. The CCD 17 photoelectrically converts an optical image formed at the image pickup surface. On the image pickup surface of the CCD 17, for example, a color separation filter 18 that performs optical color separation into red (R), green (G) and blue (B) in, for example, units of pixels is disposed.

A drive circuit 35 and a signal processing circuit 36 inside the video processor 3 to which the connector 9 is connected are connected to the CCD 17 via signal wires 19 and 20 inserted in the endoscope 2, respectively.

The drive circuit 35 applies a drive signal to the CCD 17, and the CCD 17 outputs an image pickup signal (image signal) resulting from photoelectric conversion upon the application of the drive signal to the signal processing circuit 36.

The signal processing circuit 36 generates a standard video signal for the inputted image signal, and outputs the video signal to the monitor 4. On a display surface of the monitor 4, an endoscopic image corresponding to the standard video signal is displayed.

Also, the operation section 7 of the endoscope 2 is provided with an imaging mode switching switch (or an imaging mode selection switch) 37 as an imaging mode selecting section that performs an operation to give an instruction for switching (or selecting) imaging modes. A surgeon operates the imaging mode switching switch 37, whereby an instruction signal for switching between a normal imaging mode or a broadband light imaging mode (WLI mode) using broadband light illumination provided by the first light source section 21 and a narrow band light imaging mode (NBI mode) using narrow band light illumination provided by the second light source section 22 is outputted to the control circuit 34.

The control circuit 34 controls operations of the power supply circuit 33 and the signal processing circuit 36 according to the instruction signal. It is possible that the control circuit 34 also controls an operation of the drive circuit 35.

The signal processing circuit 36 generates respective R, G and B signals according to color separation of R, G and B performed by the color separation filter 18 of the CCD 17 under the illumination with white color broadband light and outputs a color video signal to the monitor 4. Then, the monitor 4 displays a color endoscopic image as a normal image or a broadband image (WLI image).

Meanwhile, under illumination with the blue color narrow band light, the signal processing circuit 36 generates a B signal corresponding to a B component resulting from color separation performed by the color separation filter 18, and outputs a monochrome video signal including the B signal only to the monitor 4. Then, the monitor 4 displays a monochrome endoscopic image as a narrow band image (NBI image) picked up under illumination with the blue color narrow band light. Here, a black-and-white endoscopic image (NBI image) may be displayed by inputting the B signal to the R and G channels in addition to the B channel of the monitor 4.

The endoscope 2 according to the present embodiment configured as described above includes: the insertion portion 6 to be inserted into a subject; the operation section 7 provided at a proximal end of the insertion portion 6, the operation section 7 including the operation means; the first light source section 21 provided inside the operation section 7, the first light source section 21 generating first light as broadband light having a broadband wavelength characteristic covering a visible wavelength band; the light guide 27 as a light guiding section disposed so as to extend from the operation section 7 to a vicinity of the distal end portion of the insertion portion 6, the light guiding section guiding the first light emitted from the first light source section 21; the second light source section 22 provided in the vicinity of the distal end portion 11 of the insertion portion 6, the second light source section 22 generating second light as narrow band light having a narrow band wavelength characteristic; and the prism 28 provided at the distal end portion 11 of the insertion portion 6, the prism 28 including first and second entrance faces from which the first light guided by the light guiding section and the second light from the second light source section 22 enter, respectively, and including an emission face that emits light entering from the first and second entrance faces in a predetermined direction in which the illuminating window opens.

Here, the first light source section 21 generates white color light covering a visible wavelength band as the first light, and the second light source section 22 generates light in a narrow band on the short wavelength side of the visible wavelength band, as the second light.

An operation of the present embodiment configured as described above will be described with reference to FIG. 4. Upon application of power, the control circuit 34 sets a WLI mode as a predetermined imaging mode for initial setting, as illustrated in step S1.

In this case, the control circuit 34, which is the control section, controls the power supply circuit 33 so that the drive power is supplied to the white color LED 23 in the first light source section 21 and the blue color LED 25 in second light source section 22, and also controls an operation mode of the signal processing circuit 36 to be a signal processing mode for a WLI mode for broadband light (white color light).

Here, white color light from the white color LED 23 is turned into illuminating light with lack of a blue narrow band light portion, by the prism 28 including a dichroic prism, and thus, the control circuit 34 controls an operation of the power supply circuit 33 to make the white color LED 23 and the blue color LED 25 emit light simultaneously in the case of the WLI mode. In this case, the white color illuminating light with almost no lack of the blue narrow band light portion is emitted to the object side. Then, a WLI image is displayed on the monitor 4.

The surgeon observes the WLI image displayed on the monitor 4 to examine, e.g., a diseased part. In next step S2, the control circuit 34 determines whether or not an instruction to switch imaging modes is provided. If an instruction to switch imaging modes is not provided, the control circuit 34 returns to the processing in step S1.

Meanwhile, if the switching instruction is provided, as illustrated in step S3, the control circuit 34 sets an NBI mode. In this case, the control circuit 34 controls the power supply circuit 33 so that the drive power is supplied to the second light source section 22, and also controls the operation mode of the signal processing circuit 36 to be a signal processing mode for narrow band light. Then, an NBI image is displayed on the monitor 4.

Blue narrow band light largely attenuates inside a mucous membrane of a living body, and thus, only a component of light reflected from a vicinity of a superficial layer of the mucous membrane of the living body effectively enters the CCD 17 that receives the reflected light. Accordingly, an NBI image picked up by the CCD 17 under illumination with the blue narrow band light and generated by the signal processing circuit 36 becomes an image clearly indicating, e.g., flow in capillary vessels in the vicinity of the superficial layer, enabling the surgeon to observe, e.g., the flow in the capillary vessels in an easily-recognizable state.

In next step S4, the control circuit 34 determines whether or not an instruction to switch imaging modes is provided. If no instruction to switch imaging modes is provided, the control circuit 34 returns to the processing in step S3. Meanwhile, if the switching instruction is provided, the control circuit 34 proceeds to processing for setting a WLI mode in step S1.

In the present embodiment operating as described above, the second light source section 22 that generates light in a blue color narrow band on the short wavelength side of a visible wavelength band, is disposed inside the distal end portion 11 of the insertion portion 6, enabling the blue color narrow band light generated by the second light source section 22 to be emitted from the illuminating window with almost no loss when the light is guided.

Accordingly, according to the present embodiment, a decrease in light amount of narrow band light generated by the light source for narrow band light can be reduced, and illumination with broadband light for imaging can be provided without trouble. Furthermore, it is possible to select normal imaging under illumination with white color light as broadband light or imaging under illumination with narrow band light, the imaging enabling easy recognition of flow in blood vessels in the vicinity of a superficial layer of a mucous membrane of a living body such as a diseased part, with a simple configuration.

Furthermore, according to the present embodiment, even though a dichroic prism is used as the prism 28, if the WLI mode is selected, white color illuminating light is emitted to the object side with almost no lack of the blue color narrow band light portion, enabling generation of a color image with good color reproducibility of an object such as a diseased part, which is close to a case where the object is actually observed under while color light illumination.

Furthermore, according to the present embodiment, a common image pickup device can be used for the WLI mode and the NBI mode, and in the case of the NBI mode, a B signal component in the case of the WLI mode is extracted, whereby an NBI image can be generated easily.

Figure 5:
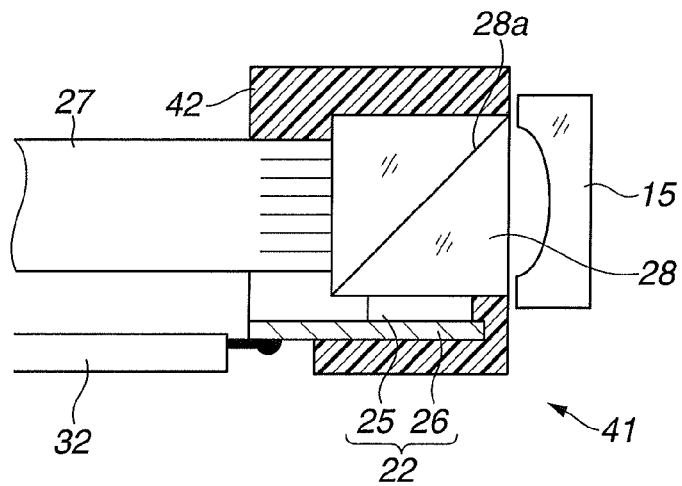
FIG. 5 is a cross-sectional diagram illustrating a configuration of a second light source unit according to a first variation of the first embodiment.

FIG. 5 illustrates a vertical cross-sectional view of a second light source unit 41 in an endoscope according to a first variation of the first embodiment.

In the present variation, a second light source unit 41 with the second light source section 22 integrated with the distal end portion of the light guide 27 and the prism 28 in the first embodiment is formed.

Figure 6A:
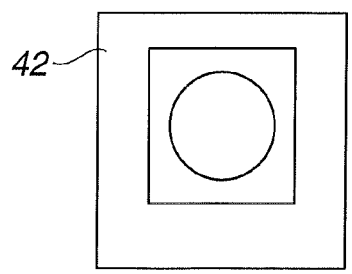
FIG. 6A is a front view of a sheathing block included in a second light source unit.
Figure 6B:
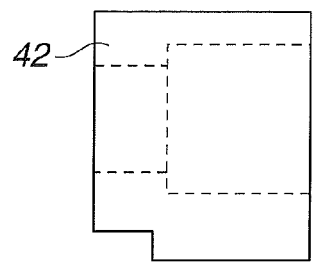
FIG. 6B is a side view of the sheathing block included in the second light source unit.
Figure 6C:
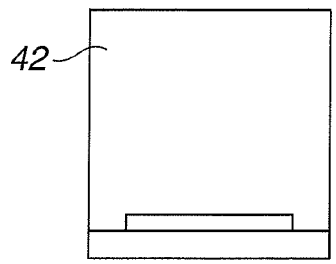
FIG. 6C is a back view of the sheathing block included in the second light source unit.

FIGS. 6A to 6C illustrate a front view, a side view and a back view of an LED sheathing block 42, respectively.

In the second light source unit 41, a prism 28 is disposed in a recess portion provided in the vicinity of a center on the front side of the LED sheathing block 42, and a blue color LED 25 and an LED substrate 26 with the blue color LED 25 mounted thereon are fixed to a bottom face (second entrance face) of the prism 28 so that an emission face of the blue color LED 25 is in close contact with the bottom face.

Also, a distal end side of a light guide 27 is inserted into a recess portion on the back side of the LED sheathing block 42 and fixed in a state in which a distal end face of the light guide 27 is in close contact with a back face (first entrance face) of the prism 28 disposed inside the recess portion.

Furthermore, a distal end of a power supply wire 32 is connected by soldering to a contact of the LED substrate 26 that is electrically connected to the blue color LED 25.

An illumination lens 15 is disposed immediately ahead of an emission face of the prism 28 or in contact with the emission face.

According to the present variation, an operation of the second light source unit 41 including a second light source section 22 can be stabilized over a long period of time.

Figure 7A:
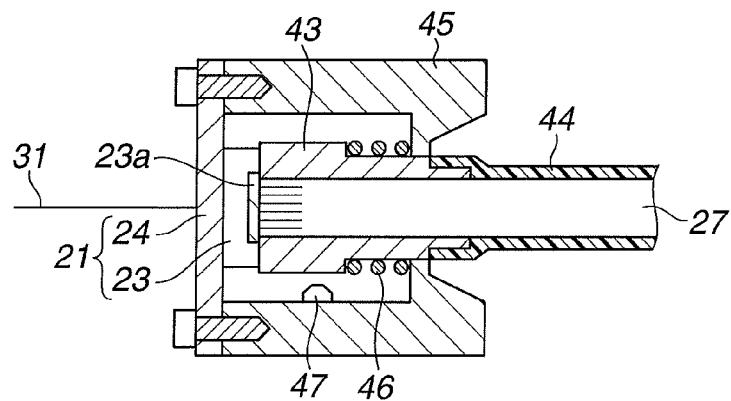
FIG. 7A is a cross-sectional diagram illustrating a structure around a first light source section in a second variation of the first embodiment.

FIG. 7A illustrates a structure around a first light source section 21 according to a second variation of the first embodiment. In the present variation, a light source fixing portion that maintains an end face of the first light source section 21 from which white color light is emitted and an end face on the entrance side of a light guide 27, which is a light guiding section, in contact with each other and fixes the end faces in such state.

Figure 7B:
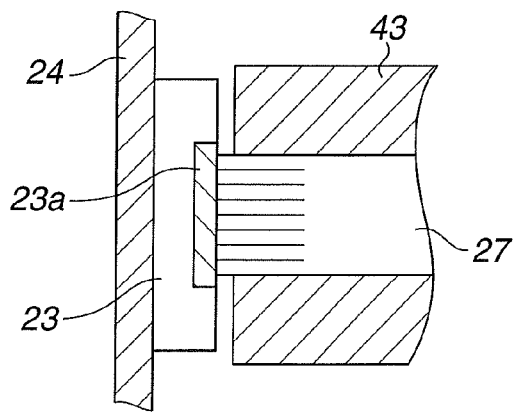
FIG. 7B is an enlarged diagram illustrating a vicinity of an end face of a light guide in FIG. 7A.

The end face on the entrance side of the light guide 27 is fixed by a light guide pipe sleeve (abbreviated as "LG pipe sleeve") 43, and a part of the light guide 27 behind the LG pipe sleeve 43 is covered by the LG sheathing tube 44. Here, the light guide 27 is processed so that the end face on the entrance side of the light guide 27 slightly protrudes from an end face of the LG pipe sleeve 43. FIG. 7B illustrates an enlarged view of such part.

Furthermore, a stepped portion is provided on the rear end side of the LG pipe sleeve 43, and on the rear end side of the stepped portion, a heatsink 45 having an inner diameter that fits an outer diameter of the stepped portion is provided. The heatsink 45 is provided so as to have a substantially cylindrical shape surrounding a white color LED 23 and the LG pipe sleeve 43, and an end face thereof can be fixed via screws to an LED substrate 24.

In the present variation, a spring 46, which is urging means, is disposed on an outer circumferential face of the stepped portion, and an end of the spring 46 is in contact with a step face of the LG pipe sleeve 43 and another end thereof is in contact with an inner face of the heatsink 45 that is opposed to the step face.

The LED substrate 24 and the heatsink 45 are fixed via screws to each other with the spring 46 in a compressed state disposed on the outer circumferential face of the stepped portion.

Thus, the spring 46 provides a light source fixing portion that fixes the end face on the entrance side of the light guide 27 and an end face of the white color LED 23 to each other in an elastically urged state so that the end face of the white color LED 23 is in contact with the end face on the entrance side of the light guide 27. In FIG. 7A, a light emitting section (emitting portion) of the white color LED 23 that actually generates white color light (or emits white color light) is indicated by reference numeral 23a. An end face of the light emitting section 23a and the end face of the light guide 27 are fixed to each other in an urged state so that the end face of the light guide 27 is in contact with the end face of the light emitting section 23a.

A plurality of adjustment screws 47 (only one of the adjustment screws illustrated in FIG. 7A) is provided in the heatsink 45, whereby adjustment for positioning can be made (by pressing the LG pipe sleeve 43) via the adjustment screws 47 so that the end face of the light guide 27 is in contact with a position of the end face of the white color LED 23.

The configuration according to the present variation enables positioning of the end face of the white color LED 23 and the end face of the light guide 27, and also enables the contact state to be maintained over a long period of time. Thus, loss in light amount of white color light from the white color LED 23 due to misalignment between the end faces can be prevented.

Accordingly, the present variation enables an operation performed by the light guide 27, which is light guiding means, to stably guide white color light generated by the white color LED 23 to be maintained over a long period of time.

Figure 8:
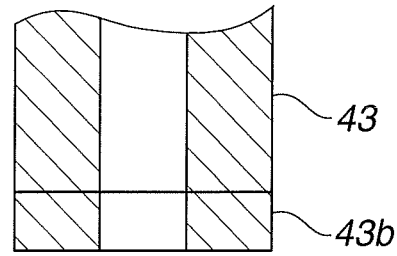
FIG. 8 is a diagram illustrating a procedure for processing for making the end face of the light guide to protrude as illustrated in FIG. 7B.
Figure 8:
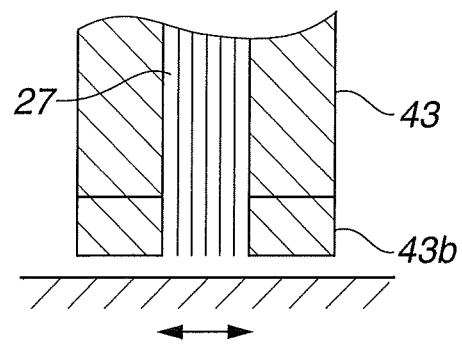
Figure 8:
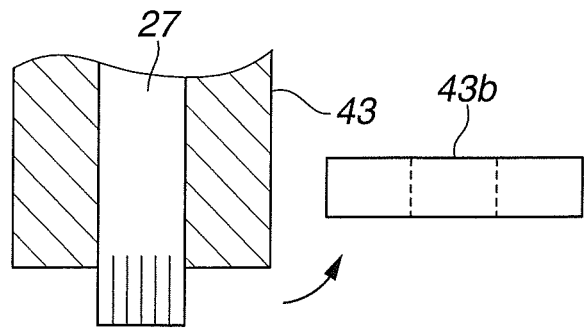

Next, a procedure for processing for making the end face of the light guide 27 slightly protrude from the end face of the LG pipe sleeve 43 as illustrated in FIG. 7B will be described with reference to FIG. 8.

As illustrated in FIG. 8(A), a second LG pipe sleeve 43b having dimensions that are the same of the LG pipe sleeve 43 is fixed on an end portion side of the LG pipe sleeve 43 (in order to fix the end portion side of the light guide 27). The second LG pipe sleeve 43b has a circular ring shape having a total length that is shorter than that of the LG pipe sleeve 43.

Next, as illustrated in FIG. 8(B), an end portion side of the light guide 27 is inserted into the LG pipe sleeve 43 and the second LG pipe sleeve 43b fixed as illustrated in FIG. 8(A) and the end portion side of the light guide 27 is fixed using an adhesive charged. Next, the end face of the light guide 27 is brought into contact with an abrading surface of, e.g., an abrasive apparatus to abrade the end face to be a smooth flat surface by means of, e.g., reciprocation as indicated by the arrow, for example.

After the abrasion, as illustrated in FIG. 8(C), the second LG pipe sleeve 43 is removed. Consequently, processing can be made so that the end face of the light guide 27 slightly protrudes from the end face of the LG pipe sleeve 43 as illustrated in FIG. 7B.

Figure 9A:
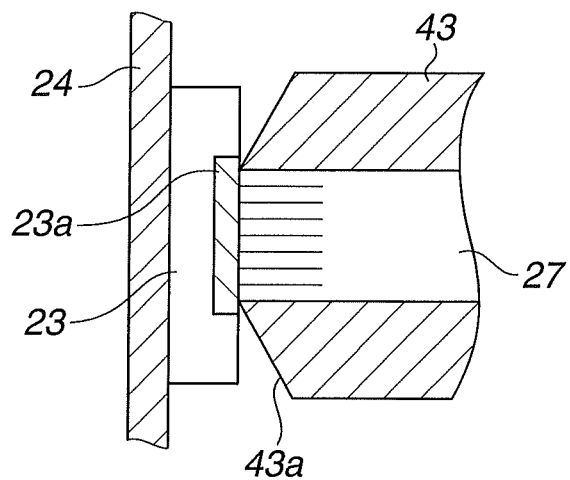
FIG. 9A is an enlarged diagram illustrating a vicinity of an end face of a light guide in the variation in FIG. 7B.

Instead of processing being performed so that the end face of the light guide 27 protruding from the end face of the LG pipe sleeve 43 in a step-like manner as illustrated in FIG. 7B, the end face of the light guide 27 may be made to protrude from a tapered surface 43a formed in the surrounding LG pipe sleeve 43 as illustrated in FIG. 9A.

Figure 9B:
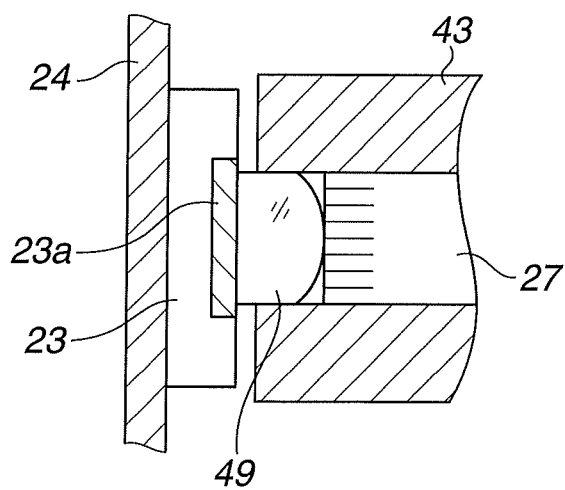
FIG. 9B is a diagram illustrating the vicinity of the end face of the light guide when a condenser lens is provided immediately ahead of the end face of the light guide.

Otherwise, a condenser lens 49 may be provided to the end face of the light guide 27 as illustrated in FIG. 9B. In FIG. 9B, a flat face, which is a front face of the condenser lens 49 fixed to the LG pipe sleeve 43, is set so as to be in contact with an end face of the white color LED 23. In this case, also, effects similar to those of the configuration in FIG. 7B are provided.

Figure 10:
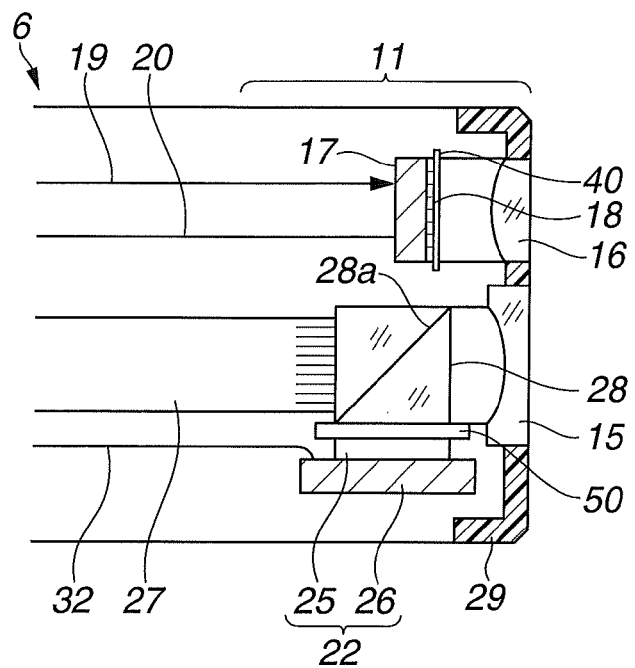
FIG. 10 is a diagram illustrating a configuration of a distal end portion of an insertion portion in a third variation of the first embodiment.

FIG. 10 illustrates a configuration of a distal end portion 11 of an insertion portion 6 according to a third variation of the first embodiment.

In the present variation a plate-like polarizer 50 is disposed between the emission face of the blue color LED 25 and the second entrance face of the prism 28 in the configuration in FIG. 2. The polarizer 50 transmits only light polarized in a predetermined direction in blue color narrow band light generated by the blue color LED 25. Also, a plate-like polarizer 40 is disposed between an objective lens 16 and a CCD 17. The remaining part of the configuration is similar to that of the first embodiment.

In this case, the polarization direction of the polarizer 50 is set so as to correspond to or be perpendicular to a polarization direction of the polarizer 40.

The present variation enables NBI using a reflected light component when an object such as a diseased part is illuminated with blue color narrow band light polarized in a predetermined direction. Otherwise, effects similar to those of the first embodiment are provided.

Although the above embodiment or variations have been described in terms of the configuration in which a common prism 28 is used to make broadband light or narrow band light emit from the emission face side of the prism 28, and a configuration such as a fourth variation, which is described below, may be employed.

Figure 11:
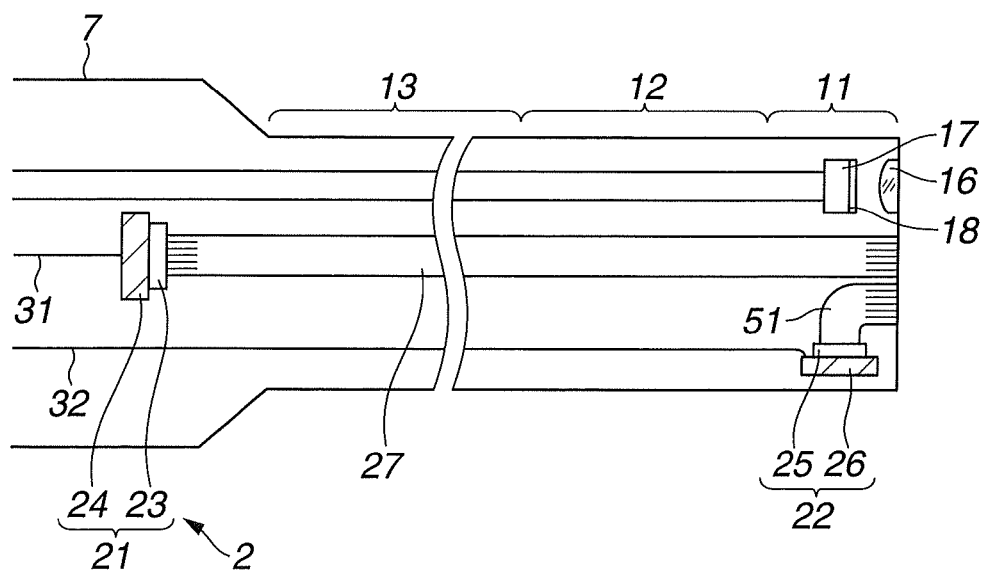
FIG. 11 is a diagram illustrating a configuration of a distal end portion of an insertion portion in a fourth variation of the first embodiment.

In the fourth variation illustrated in FIG. 11, the distal end of the light guide 27 is fixed to a first illuminating window in the first embodiment in FIG. 1. Also, an end face of a light guide 51, which is light guiding means flexed in an L-shape, is brought into close contact with the emission face of the blue color LED 25 in the second light source section disposed inside the distal end portion 11, and another end face thereof is fixed to a second illuminating window.

In other words, in the present variation, in the case of a WLI mode, broadband light is generated by a first light source section 21 and guided by a light guide 27 and is emitted from the first illuminating window, and in the case of an NBI mode, narrow band light is generated by a second light source section 22 and guided by the light guide 51 having a short length and is emitted from the second illuminating window. The first illuminating window and the second illuminating window are formed adjacent to each other at a distal end face.

In the case of the present variation, the light guide 51 is used as light guiding means for the second light source section 22; however, the length of the light guide 51 is short enough to suppress loss caused by light guiding by the light guide 51 to be sufficiently small.

Illumination lenses may further be provided in respective distal end faces of the light guide 27 and the light guide 51.

Figure 12:
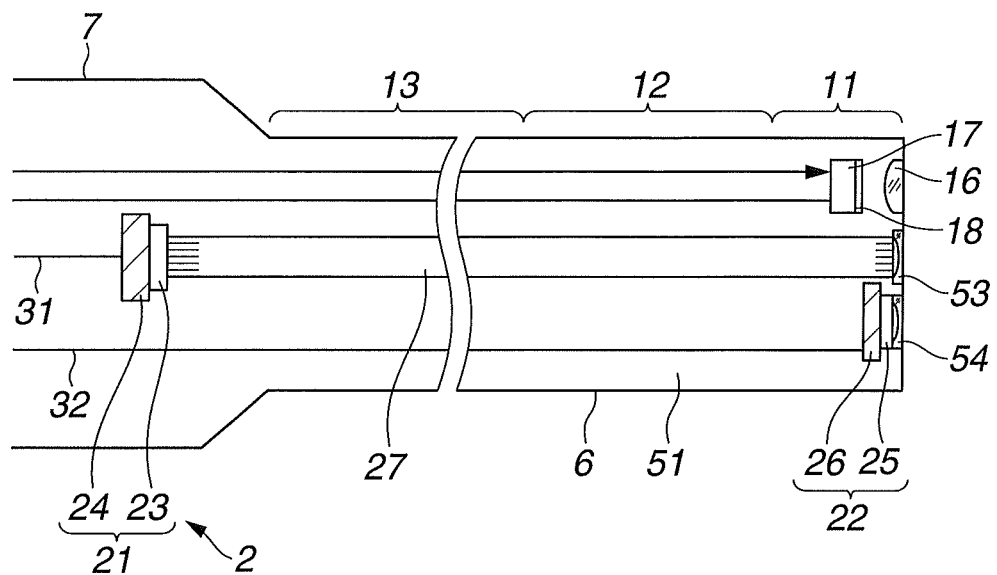
FIG. 12 is a diagram illustrating a configuration of a distal end portion of an insertion portion in a fifth variation of the first embodiment.

Also, where a first illuminating window and a second illuminating window are provided as in the fourth variation, a configuration of a fifth variation, which is illustrated in FIG. 12, may be employed.

In an endoscope 2, which is illustrated in FIG. 12, a first illumination lens 53 is attached to the first illuminating window illustrated in FIG. 11, and broadband light emitted from a distal end face of the light guide 27 is emitted via the first illumination lens 53 opposed to the distal end face.

Furthermore, a second illumination lens 54 is attached to a second illuminating window, and a blue color LED 25 included in a second light source section 22 is disposed so that an emission face of the blue color LED 25 is opposed to the second illumination lens 54.

Figure 13A:
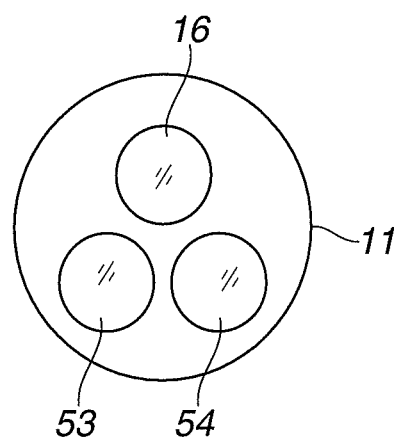
FIG. 13A is a front view of the distal end portion in FIG. 12.

FIG. 13A illustrates a front view of the distal end portion 11 in FIG. 12.

In the present variation, broadband light including white color light, and narrow band light are emitted from different illuminating windows.

In the present variation, light emitted by the blue color LED 25 is emitted via the second illumination lens 54 without using light guiding means.

In the above-described first embodiment, at the time of switching between the WLI mode and the NBI mode, high-speed switching for illumination (light emission) according to the respective imaging modes and signal processing can be achieved without the need to provide a mechanical movable portion.

Thus, an illumination period for the WLI mode (abbreviated as "WLI period") and an illumination period for the NBI mode (abbreviated as "NBI period") can alternately be switched from one to the other, for example, each frame period, to set an imaging mode enabling simultaneously display of a WLI image and an NBI image (with a time lag corresponding to one frame period). Then, it is also possible to set a WLI/NBI mode as the imaging mode, enabling simultaneous display of a WLI image and an NBI image on the monitor 4.

Figure 13B:
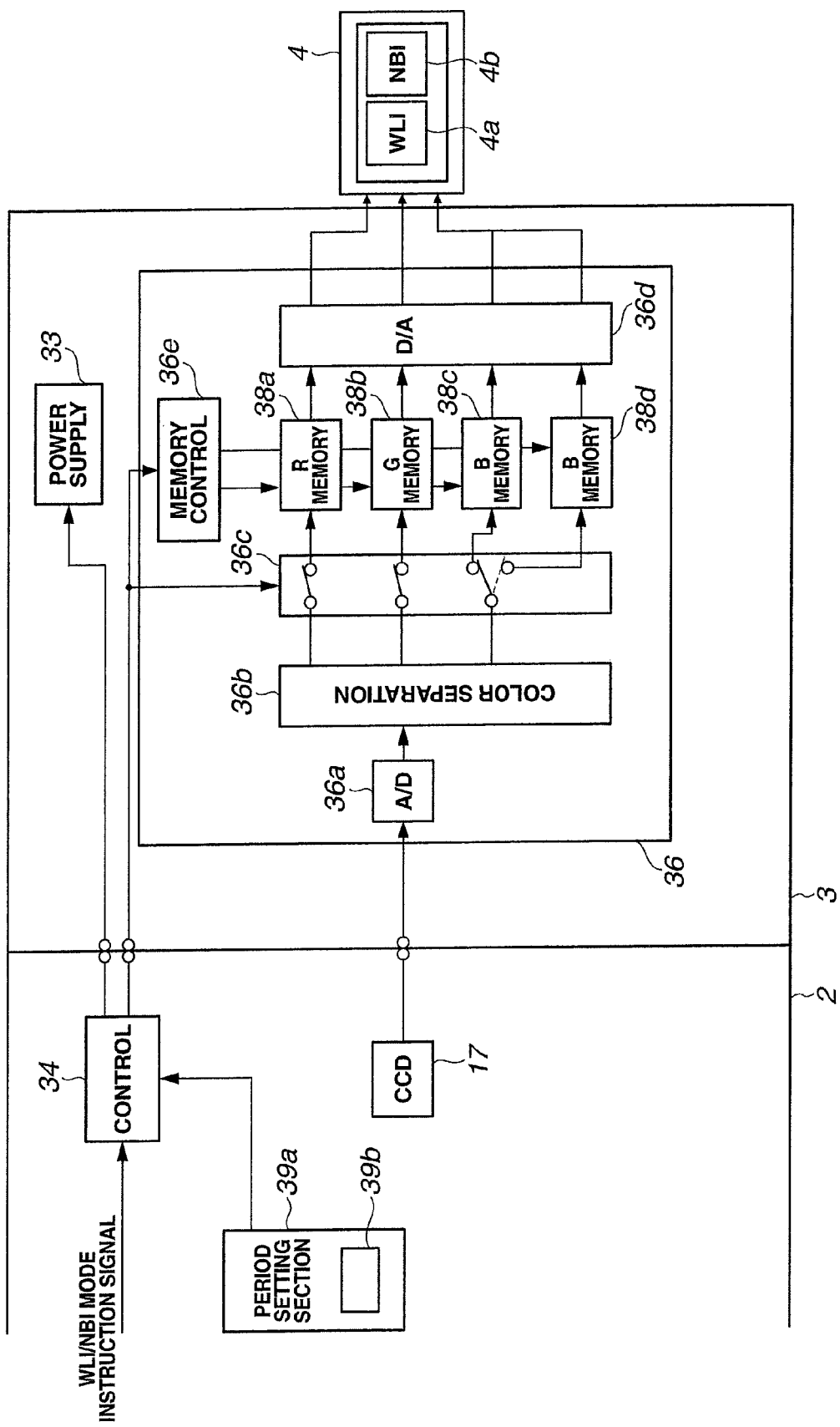
FIG. 13B is a configuration of a signal processing circuit in a sixth variation of the first embodiment.

FIG. 13B illustrates a configuration of a signal processing circuit 36 in a sixth variation providing the WLI/NBI mode. Furthermore, FIG. 13C illustrates a timing chart for operation illustration.

An image signal picked up by the CCD 17 is subjected to extraction of a signal component only by a non-illustrated correlated double sampling circuit, and then the signal component is converted into a digital image signal by an A/D conversion circuit 36a and inputted to a color separation circuit 36b.

The color separation circuit 36b separates the inputted image signal into R, G and B signal components according to an arrangement in a color separation filter 18, and the R, G and B signal components are outputted to a R memory 38a, a G memory 38b, a B memory 38c and a B memory 38d via a changeover switch 36c including, e.g., analog switches.

The R memory 38a, the G memory 38b and the B memory 38c are memories storing broadband R, G and B signals, respectively, and the B memory 38d is a memory storing narrow band B signals.

The changeover switch 36c is made to change over every frame period by a control circuit 34 to which an instruction signal for the WLI/NBI mode is inputted.

The on or selection state of the changeover switch 36c indicated by the solid lines in FIG. 13B indicates a state in which an image signal picked up in a WLI period is inputted, and broadband R, G and B signals are stored in the R memory 38a, the G memory 38b and the B memory 38c, respectively.

Meanwhile, the selection state of the changeover switch 36c indicated by dotted lines indicates a state in which an image signal picked up in an NBI period is inputted, and in this case, a narrow band B signal is stored in the memory 38d. Here, signal processing performed by the signal processing circuit 36 on image signals picked up in a WLI period and an NBI period take place immediately after the WLI period and the NBI period, respectively.

It is possible to enable the WLI/NBI mode to be selected by, for example, a switch provided in an imaging mode switching switch 37 or a switch dedicated to selection of the WLI/NBI mode may be provided in the endoscope.

The image signals stored in the R memory 38a, the G memory 38b, the B memory 38c and the B memory 38d are read by a memory control circuit 36e in each frame period and inputted to a D/A conversion circuit 36d.

However, the control circuit 34 controls an operation of the memory control circuit 36e so that the B signal, which is read from the memory 38d, is read at a timing delayed by around one-half of one horizontal period compared to the R, G and B signals simultaneously read from the R memory 38a, the G memory 38b and the B memory 38c, respectively.

As a result of such control, the signal processing circuit 36 performs processing for generating image signals for a composite image in which two images are disposed adjacent to each other in a horizontal direction.

The D/A conversion circuit 36d converts the inputted digital image signals into analog video signals (image signals) and then outputs the analog video signals to R, G and B channels in a monitor 4. Then, the monitor 4 simultaneously displays a WLI image (abbreviated as "WLI") 4a and an NBI image (abbreviated as "NBI") 4b adjacent to each other in the horizontal direction.

In the configuration in FIG. 13B, the B signal from the B memory 38d is add to the B signal from the B memory 38c and inputted to the B channel in the monitor 4 and the NBI image 4b is displayed in blue color.

FIG. 13C illustrates an illustrative diagram of an operation of the present variation when the WLI/NBI mode is selected. Control is performed so that in WLI periods such as a first frame period T1, a third frame period T3, . . . , the white color LED 23 and the blue color LED 25 simultaneously emit light, and in NBI periods such as a second frame period T2, a fourth frame period T4, . . . , a blue color LED 25 emits light.

At a timing of an end of the first frame period T1, a drive signal is applied to the CCD 17, R, G and B signals picked up in the first frame period T1 (R(T1), G(T1) and B(T1) in FIG. 13C) are stored in the R, G and B memories 38a to 38c, respectively. The image signals are retained in the memories until signals picked up in a next WLI period (third frame period T3) are inputted (written over the image signals).

Meanwhile, at a timing of an end of the second frame period T2, the drive signal is applied to the CCD 17 and a B signal picked up in the second frame period T2 (B(T2) in FIG. 13C) is stored in the B memory 38d. The B signal is retained in the memory until an image signal picked up in a next NBI period (third frame period T3) is inputted (written over the B signal).

In each frame period, the image signals stored in the R, G and B memories 38a to 38c and the B memory 38d are read, and on a display surface of the monitor 4, a WLI image 4a and an NBI image 4b are simultaneously displayed.

According to the present variation, a WLI image 4a and an NBI image 4b can simultaneously be displayed, and thus, a part observed in the NBI image 4b can be reviewed in the WLI image 4a, facilitating, e.g., diagnosis. Furthermore, in periods in which no WLI image 4a is acquired, the white color LED 23 does not emit light, enabling power saving.

Where the blue color LED 25 emits light as indicated by the alternate long and two short dashes lines in FIG. 13C, the light emission intensity may be increased in NBI periods compared to WLI periods. As a result of such light emission driving, a clearer NBI image 4b can be acquired, facilitating, e.g., diagnosis.

Furthermore, where the WLI/NBI mode is set, such case is not limited to alternate changeover of every frame period, but a period setting section 39*a* (see FIG. 13B) may be provided in, e.g., the operation section 7 of the endoscope so that a user such as a surgeon can change and set from/to a WLI period to/from an NBI period.

For example, where a surgeon mainly uses the WLI mode and makes NBI images 4*b* be displayed for reference, it is possible to provide longer WLI periods and shorter NBI periods.

Furthermore, where a surgeon mainly uses the NBI mode and makes WLI images 4*a* be displayed for reviewing a site to be observed using the WLI images 4*a*, it is possible to provide longer NBI periods and shorter WLI periods.

The WLI periods and the NBI periods can be changed and set as described above, enabling enhancement of the operability for a surgeon to use.

Furthermore, when the WLI/NBI mode is set, an operation period setting section 39*b* may be provided so as to set an operation period of the WLI/NBI mode. For example, it is possible to temporarily set the WLI/NBI mode for an operation period set by the operation period setting section 39*b* from the state in which the WLI mode or the NBI mode is used, and after the elapse of the operation period, returns the mode in use to the WLI mode or the NBI mode. In this case, also, the operability for a surgeon to use can be enhanced.

Second Embodiment

Figure 14A:
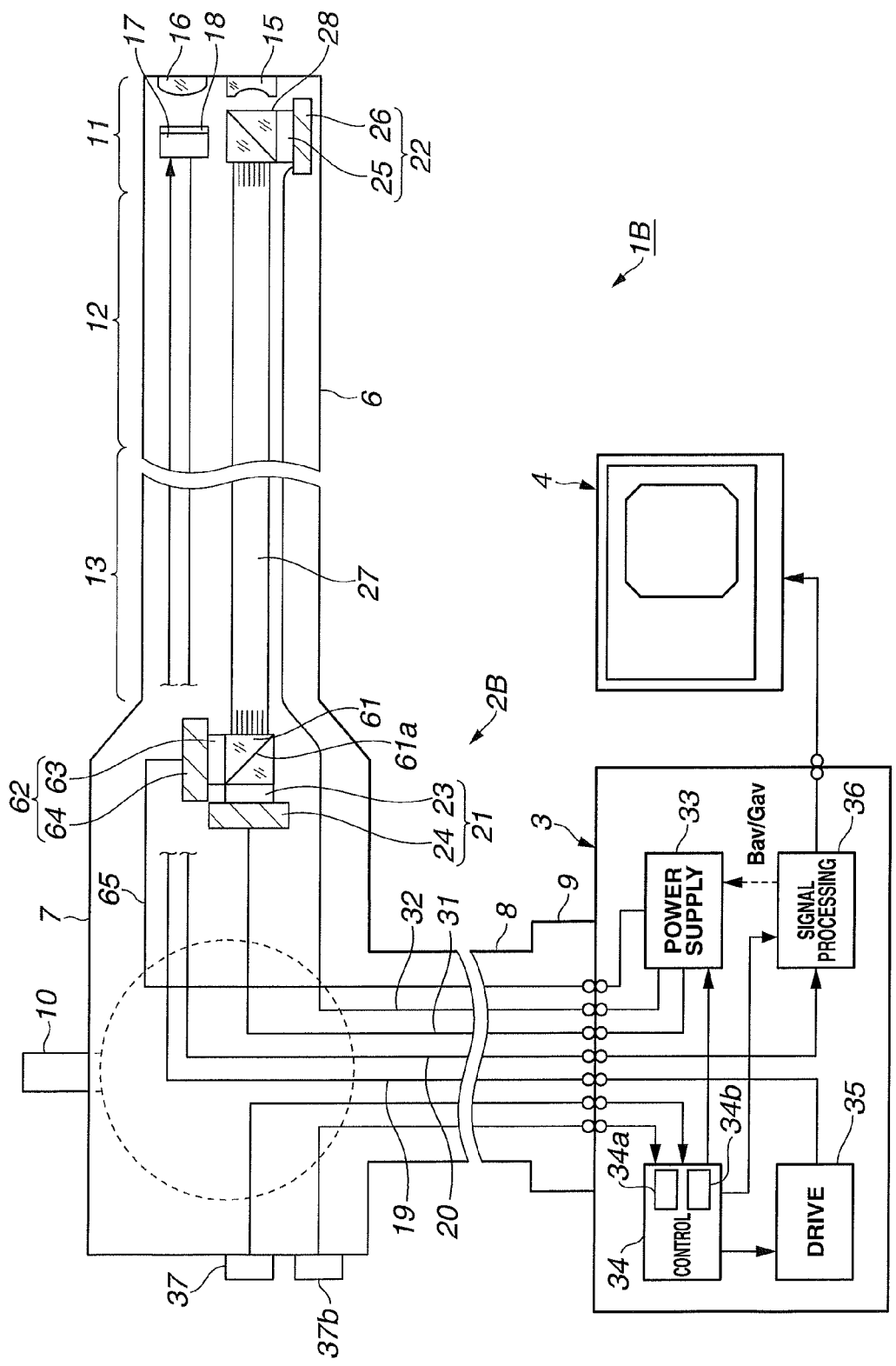
FIG. 14A is a diagram illustrating an overall configuration of an endoscope apparatus including a second embodiment of the present invention.

FIG. 14A illustrates a configuration of an endoscope apparatus 1B including a second embodiment of the present invention. An endoscope 2B in the present embodiment has a configuration resulting from the first light source section 21 in the operation section 7 of the endoscope 2 illustrated in FIG. 1 being varied.

In the endoscope 2B, a prism 61 is disposed between an emission face of a white color LED 23 in a first light source section 21 and an end face of a light guide 27 (from which light enters), and furthermore, a third light source section 62 that generates narrow band in a green color wavelength band, that is, green color narrow band light, is provided. It is also possible to define that the first light source section 21 includes the third light source section 62. Also, as described later with reference to FIG. 18, the first light source section 21 can be configured so as to selectively generate green color narrow band light from white color light.

The third light source section 62 includes a green color LED 63 that generates green color narrow band light, and a LED substrate 64 with the green color LED 63 mounted thereon. The LED substrate 64 is connected to a power supply circuit 33 via a power supply wire 65, and a control circuit 34 controls a light emission operation of the third light source section 62.

The emission face of the white color LED 23 is in close contact with a first entrance face of the prism 61 including a dichroic prism, and an emission face opposed to the first entrance face is in close contact with the end face of the light guide 27.

Figure 15:
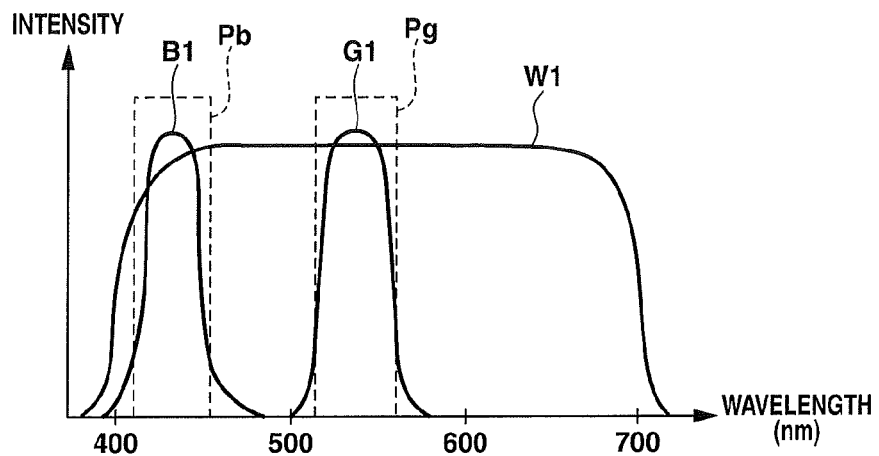
FIG. 15 is a diagram illustrating characteristics of, e.g., green color narrow band light generated by a third light source section.

Furthermore, the third light source section 62 is provided on a second entrance face of the prism 61 in such a manner that an emission face of the green color LED 63 is in close contact with the second entrance face. FIG. 15 illustrates a characteristic of green color narrow band light (G1 in FIG. 15) generated by the green color LED 63 in the third light source section 62.

Here, the prism 61 includes a dichroic prism set to have a characteristic of selectively reflecting, for example, the green color narrow band light illustrated in FIG. 15 and selectively transmitting broadband light of white color (or over a visible wavelength band) other than the green color narrow band light.

More specifically, a dielectric film 61*a* set to have a characteristic Pg of selectively reflecting the green color narrow band light indicated by a dotted line in FIG. 15 is formed on inclined joining surfaces of two triangular prisms included in the prism 61. The white color LED 23 in the first light source section 21 and a blue color LED 25 in a second light source section 22 have light emission characteristics that are the same as those of the first embodiment. Since green color narrow band light is on the long wavelength side compared to blue color narrow band light, when green color narrow band light is guided by the light guide 27, which is a light guiding section, loss in light amount of the green color narrow band light is not larger compared to the case of blue color narrow band light (even if a special light guide is not employed for the light guide 27).

In the present embodiment, where the NBI mode is set, the second light source section 22 and the third light source section 62 are made to emit light, enabling obtainment of an NBI image using both the blue color narrow band light and the green color narrow band light.

In this case, the signal processing circuit 36 generates a B signal and a G signal corresponding to B and G color separation components according to a color separation filter 18 under illumination with blue color and green color narrow band light, and outputs a video signal including the B signal and the G signal to B and G channels in a monitor 4. The monitor 4 displays an endoscopic image according to the B signal and the G signal picked up using the narrow band light.

Furthermore, in the present embodiment, in the case of an NBI mode, a function that adjusts or controls the blue color narrow band light from the blue color LED 25 and the green color narrow band light from the green color LED 63, which are emitted from an illuminating window via a prism 28, maintain a predetermined spectral characteristic (more specifically, a light amount ratio between the blue color narrow band illuminating light and the green color narrow band illuminating light to be a predetermined value or a constant value) is provided.

As illustrated in FIG. 14A, for example, an adjustment switch 37*b* for adjusting the light amount ratio is provided in the operation section 7, and an instruction signal from the adjustment switch 37*b* is inputted to a control circuit 34. The adjustment switch 37*b* includes, for example, a first switch that performs an operation to give an instruction to increase and decrease an amount of light emitted by the blue color LED 25 or a second switch that performs an operation to give an instruction to increase and decrease an amount of light emitted by the green color LED 63. Here, the adjustment switch 37*b* may include functions of both switches.

A surgeon can increase/decrease an amount of the blue color narrow band light from the blue color LED 25 or an amount of the green color narrow band light from the green color LED 63, which is emitted from the illuminating window, via the control circuit 34 by turning on/off the first switch or the second switch, and thus, adjusts power of drive power supplied from a power supply circuit 33 to both the light source sections 22 and 62 so that a predetermined light amount ratio between both blue color narrow band light and green color narrow band light is maintained by increasing/decreasing at least one of both blue color narrow band light and green color narrow band light.

Alternatively, it is possible that: an non-illustrated sensor that detects a light amount is disposed so as to be opposed to the illuminating window; an output signal from the sensor is inputted to the control circuit 34; and the control circuit 34 monitors the output signal from the sensor in response to an instruction signal from the adjustment switch 37b, and adjusts or controls power of the drive power from the power supply circuit 33 to both light source sections 22 and 62 so that a predetermined light amount ratio between both blue color narrow band light and green color narrow band light is maintained.

As described above, the control circuit 34 has a function of a light amount adjusting section 34a that makes adjustment so that there is a predetermined light amount ratio between the blue color narrow band light and the green color narrow band light (in other words, a constant light amount ratio is provided).

Furthermore, as described later with reference to, e.g., FIG. 19A, the control circuit 34 has a function of a lighting timing control section 34b that performs timing control so as to achieve simultaneous lighting (or light emission) for a predetermined period in imaging mode switching (selection).

Figure 14B:
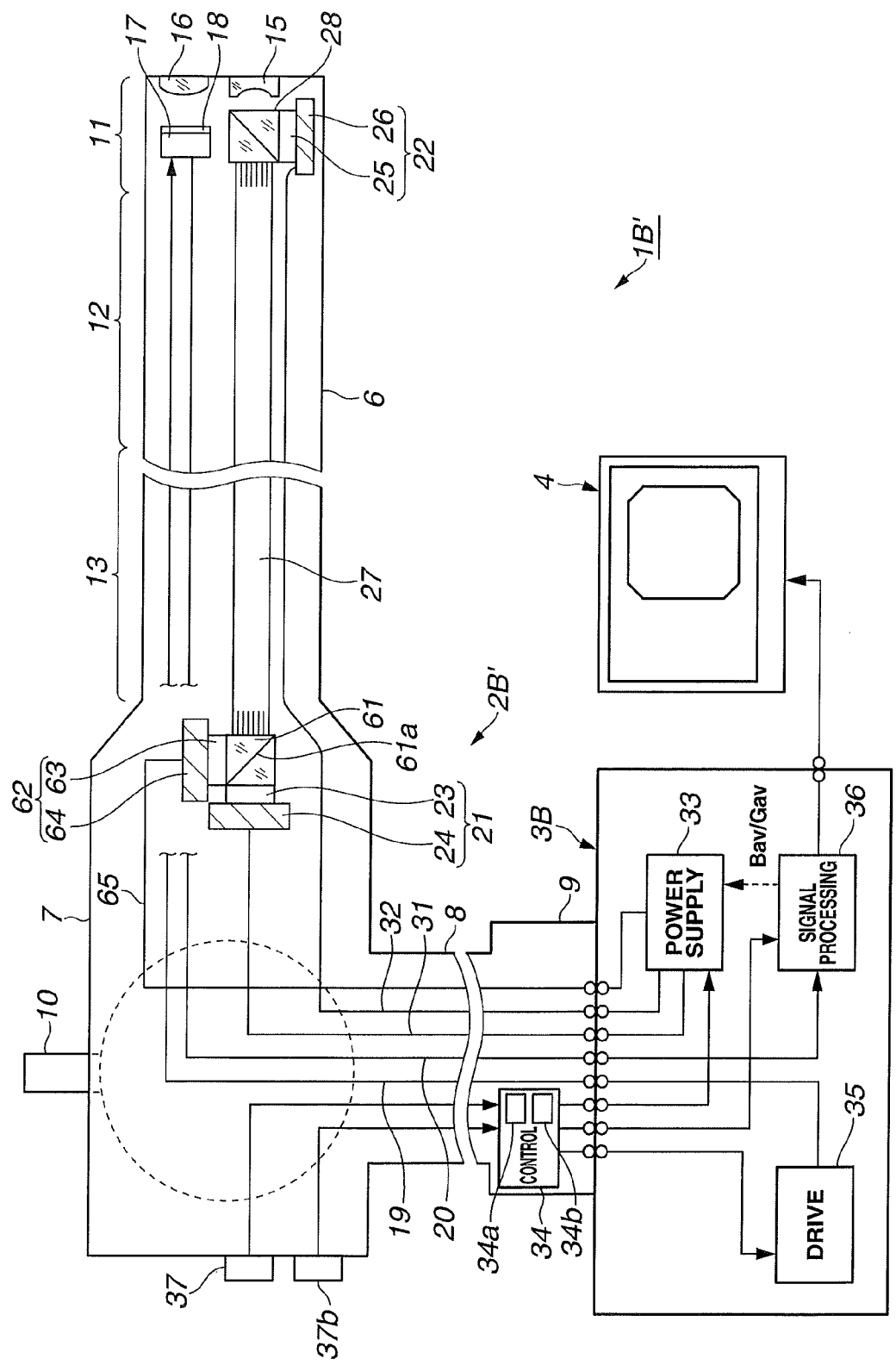
FIG. 14B is a diagram illustrating an overall configuration of an endoscope apparatus including a first variation of the second embodiment.

Although FIG. 14A illustrates a configuration in which the control circuit 34 is provided inside a processor 3, as illustrated in FIG. 14B, like an endoscope 2B' according to a first variation, a configuration of an endoscope apparatus 1B' in which a control circuit 34 is provided inside the endoscope 2B'. In FIG. 14B, a control circuit 34 is provided inside, for example, a connector 9 in the endoscope 2B', and the processor 3B includes a power supply circuit 33, a drive circuit 35 and a signal processing circuit 36 controlled by the control circuit 34. Other components in FIG. 14B are the same as those in FIG. 14A, and thus, are provided with same reference numerals as those in FIG. 14A and a description thereof will be omitted.

Figure 16:
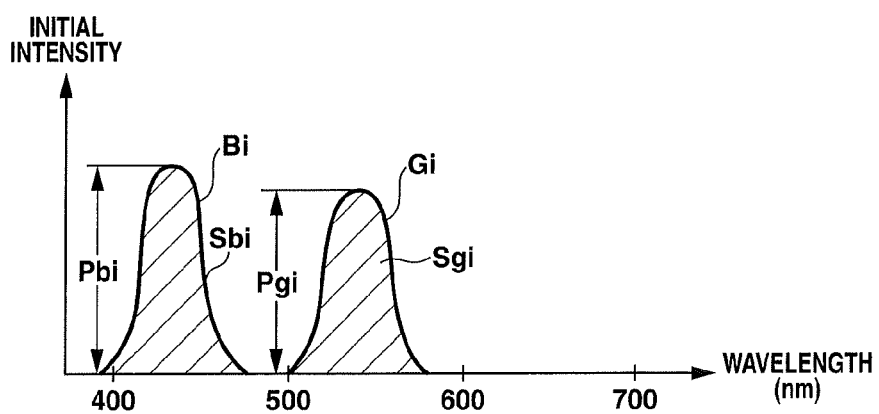
FIG. 16 is a diagram illustrating light amount adjustment made by a light amount adjusting section.
Figure 16:
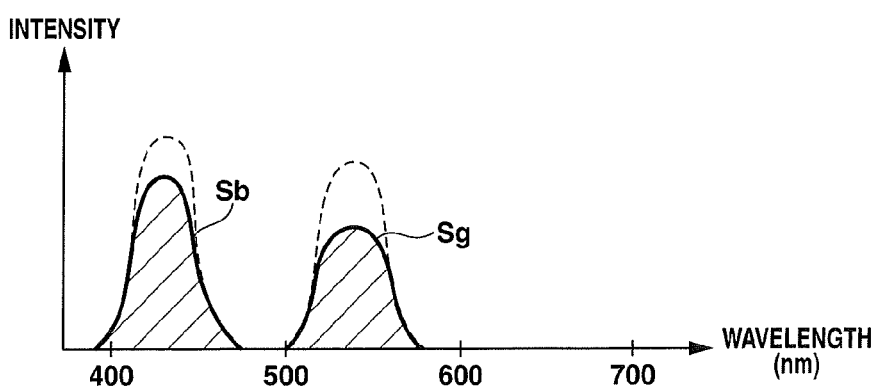

FIG. 16 illustrates diagrams illustrating light amount adjustment made by the light amount adjusting section 34a.

The diagram on the upper side of FIG. 16 illustrates characteristics of an intensity (initial intensity) of blue color narrow band light from the blue color LED 25 and an intensity (initial intensity) of green color narrow band light from the green color LED 63 in an initial state.

Also, the shadings indicate the respective areas of the intensity of the blue color narrow band light and the intensity of the green color narrow band light, and where the areas of the former and the latter are Sbi and Sgi, respectively, the area ratio is Sbi:Sgi.

Where the intensities (according to the blue color LED 25 and the green color LED 63) lower due to long-term use as illustrated on the lower side of FIG. 16, the light amount adjusting section 34a adjusts the drive power (from the power supply circuit 33) for driving the blue color LED 25 to emit light and the drive power for the green color LED 63 so that the intensity ratio between both blue color narrow band light and green color narrow band light is the light amount ratio illustrated on the upper side of FIG. 16.

In the above example, even where the intensities lower due to long-term use (where, for example, the areas of the intensities are Sb and Sg, respectively, as illustrated in FIG. 16), the drive power adjustment is made so that the ratio of the intensities is constant, specifically, a constant area ratio of Sbi:Sgi, which is the same as that in the initial state.

Where the light amount ratio is adjusted to be constant, peak values may be adjusted to be constant in addition to the adjustment made using the area ratio. For example, where peak values of the respective intensities of the blue color narrow band light and the green color narrow band light illustrated on the upper diagram in FIG. 16 are Pbi and Pgi, if the intensities lower due to long-term use as indicated on the lower side of FIG. 16, adjustment may be made so that the ratio between the peak values of the intensities is Pbi:Pgi.

Where the light amount ratio is adjusted as described above, it is possible to detect that hem parts of the blue color narrow band light and the green color narrow band light do not overlap each other and adjust the light amount ratio within the range in which such overlap does not occur. In the present embodiment, because of use of narrow band light, in many cases, the overlap can be avoided where center wavelengths of the blue color narrow band light and the green color narrow band light are not close to each other. However, if the center wavelengths are close to each other, existence or no existence of the overlap may be detected and the light amount ratio may be adjusted within the range in which the overlap does not occur.

Furthermore, as indicated by the dotted line in the processor 3 in FIG. 14A, it is possible that the signal processing circuit 36 creates respective average luminances Bay and Gay from a B signal and a G signal, and outputs a ratio Bay/Gay between the average luminances as an adjustment signal to the power supply circuit 33 to adjust the drive power for making the blue color LED 25 to emit light and the drive power for making the green color LED 63 to emit light so as to maintain a light amount ratio set in advance. In this case, light adjustment may be performed so as to obtain an image with proper brightness.

Also, adjustment may be made so that the light amount ratio is constant as described above even if the light guide 27 is broken. Furthermore, for a transmittance of the light guide 27, a transmittance according to emission wavelengths of the white color LED 21 and the green color LED 63 may be used. Alternatively, the light guide 27 may be formed by randomly bundling light guide fibers having different transmittances.

The present embodiment with such configuration enables a surgeon to properly observe, e.g., a diseased part inside a subject in a WLI mode and an NBI mode as described with reference to FIG. 4 in the first embodiment.

Figure 17:
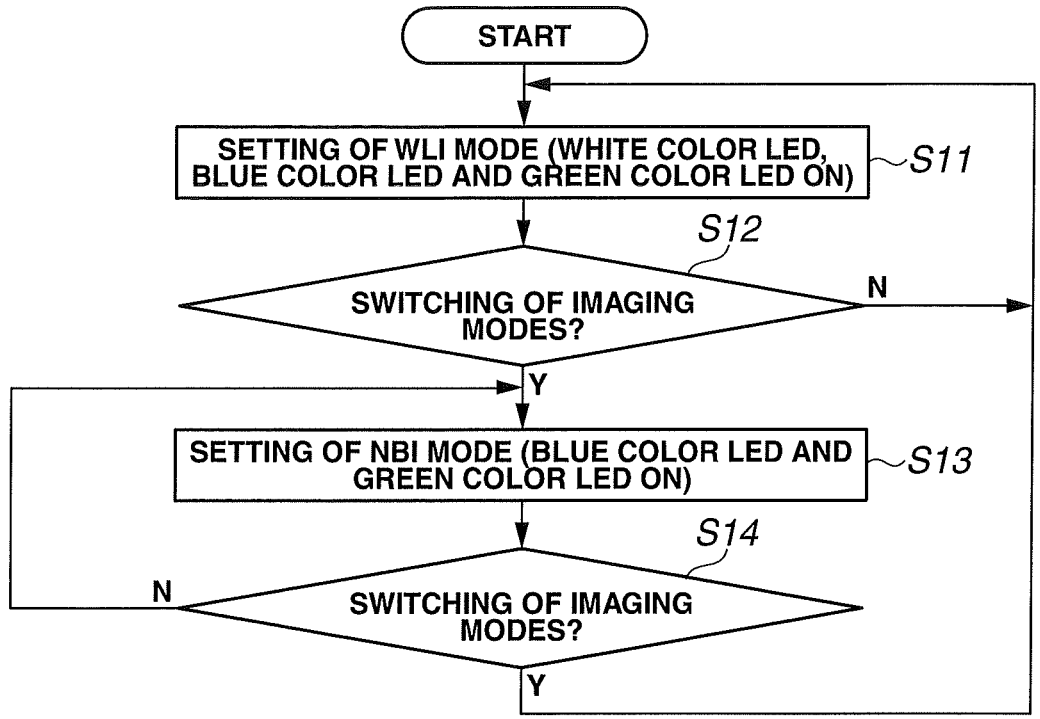
FIG. 17 is a flowchart illustrating an operation of the second embodiment of the present invention.

FIG. 17 is a diagram illustrating an operation of the endoscope apparatus 1B according to the present embodiment. An operation of the endoscope apparatus 1B' including the first variation is illustrated in FIG. 17. An operation of the present embodiment is similar to that in FIG. 4.

Figure 4:
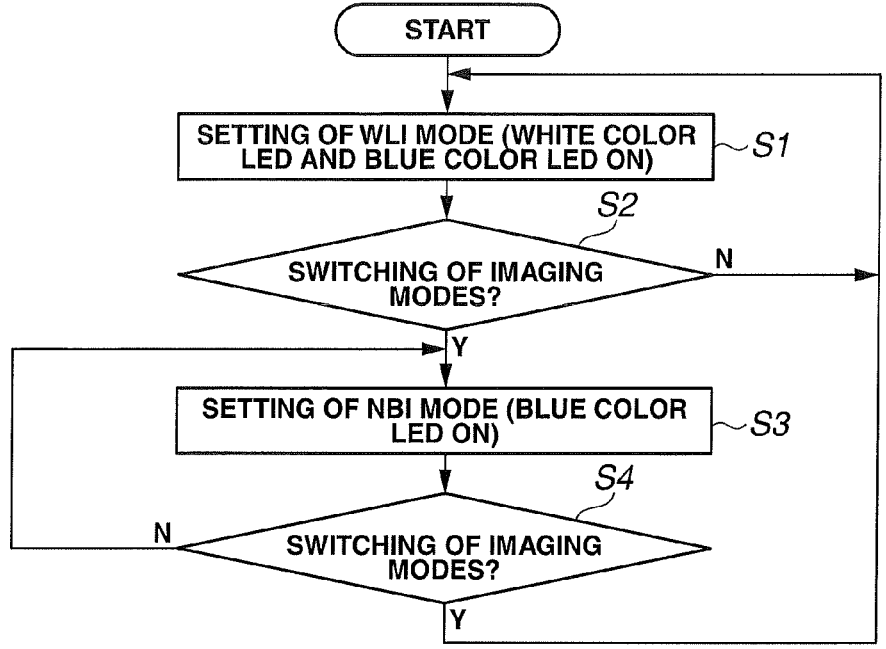
FIG. 4 is a flowchart illustrating an operation of the first embodiment.

Upon application of power, in step S11, the control circuit 34 sets, for example, a WLI mode as a predetermined imaging mode for initial setting as in step S1 of FIG. 4.

In the present embodiment, the control circuit 34 controls the power supply circuit 33 so that drive power is supplied to the white color LED 23 of the first light source section 21, the blue color LED 25 of the second light source section 22 and the green color LED 63 of the third light source section 62, and also controls an operation mode of the signal processing circuit 36 to be a signal processing mode for broadband light.

A surgeon observes or diagnoses, e.g., a diseased part in the WLI mode. In next step S12, the control circuit 34 determines whether or not an instruction to switch imaging modes is provided. If no instruction to switch imaging modes is provided, the control circuit 34 returns to the processing in step S11.

Meanwhile, if the switching instruction is provided, the control circuit 34 sets an NBI mode as illustrated in step S13. In this case, the control circuit 34 controls the power supply circuit 33 so that drive power is supplied to the blue color LED 25 of the second light source section 22 and the green color LED 63 of the third light source section 62, and also controls the operation mode of the signal processing circuit 36 to be a signal processing mode for narrow band light.

In the NBI mode, the surgeon can observe, e.g., capillary vessels in a superficial layer of a diseased part and flow in vessels somewhat deeper than the capillary vessels in a clear and easily recognizable state.

In next step S14, the control circuit 34 determines whether or not an instruction to switch imaging modes. If no instruction to switch imaging modes is provided, the control circuit 34 returns to the processing in step S13. Meanwhile, if the switching instruction is provided, the control circuit 34 proceeds to the processing for setting the WLI mode in step S11.

In the present embodiment operating as described above, as in the first embodiment, the second light source section 22 that generates blue color narrow band light is disposed inside a distal end portion 11 of an insertion portion 6, and thus, blue color narrow band light generated by the second light source section 22 can be emitted from the illuminating window with almost no loss when the blue color narrow band light is guided.

Accordingly, according to the present embodiment, as in the first embodiment, a decrease in light amount of narrow band light generated by a narrow band light source can be reduced, and illumination for imaging under broadband light can be provided without trouble.

Furthermore, in the first embodiment, in the case of an NBI mode, imaging using blue color narrow band light only can be performed; however, in the present embodiment, imaging using both blue color narrow band light and green color narrow band light can be performed.

The present embodiment enables imaging in an easily recognizable state of flow of thicker vessels on the deeper side in a vicinity of a superficial layer of a mucous membrane of a living body using green color narrow band light in addition to flow of thin vessels such as capillary vessels in the vicinity of the superficial layer using blue color narrow band light.

Furthermore, in the present embodiment, adjustment or control is performed so that a predetermined light amount ratio (or a constant light amount ratio) between blue color narrow band light and green color narrow band light from the green color LED 63 is maintained, and thus, even if the NBI mode is used over a long period of time, since there is no change in the light amount ratio, it is possible to prevent change in characteristics such as color tone of a resulting NBI image.

In the case of the NBI mode in the present embodiment, it is possible that a B signal and a G signal obtained using blue color narrow band light and green color narrow band light is converted from signals of two colors, i.e., B and G to signals of three colors by a color conversion circuit provided in the signal processing circuit 36 and displayed on the monitor 4.

Also, in the present embodiment, it is possible to enable selection of imaging using blue color narrow band light only and imaging using green color narrow band light only in the case of the NBI mode.

Figure 18:
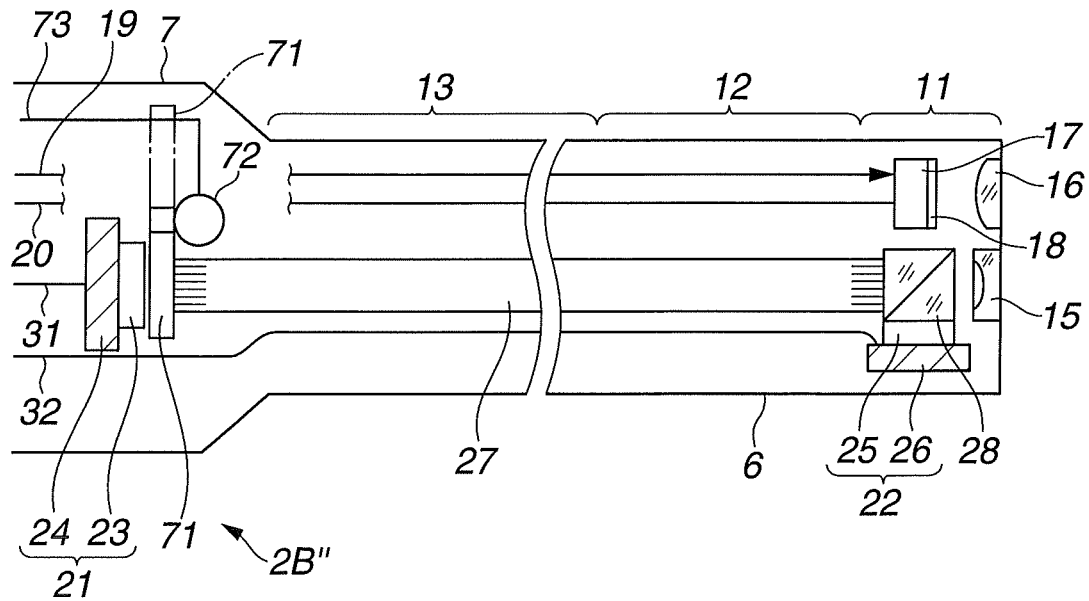
FIG. 18 is a diagram illustrating a configuration of a part of an endoscope according to a second variation of the second embodiment.

FIG. 18 illustrates a configuration in a vicinity of a second light source section in an endoscope 2B" in a second variation of the second embodiment. A gap portion is formed between the emission face of the blue color LED 23 in the second light source section 21 and the rear end face of the light guide 27 illustrated in FIG. 14A, and a green color narrow band filter 71 that selectively transmits green color narrow band light only is removably disposed in the gap portion.

The green color narrow band filter 71 is driven to enter a state in which the green color narrow band filter 71 is disposed in the gap portion (position indicated by solid lines in FIG. 18) and a state in which the green color narrow band filter 71 is retracted from the gap portion as indicated in alternate long and one short dashes lines, by, for example, a gear-equipped motor 72 as drive means. An operation of the gear-equipped motor 72 is controlled by a control signal provided from a control circuit 34 through a signal wire 73.

Where a WLI mode is set, the control circuit 34 sets the green color narrow band filter 71 to a retracted state (in FIG. 18, the green color narrow band filter 71 enters a state indicated by the alternate long and short dash lines). In this case, broadband light, which is white color light from the white color LED 23, enters a rear end face of the light guide 27 and the guided broadband light is emitted from a distal end face thereof.

Meanwhile, where the NBI mode is set, the control circuit 34 sets the green color narrow band filter 71 to be in a state in which the green color narrow band filter 71 is disposed in the gap portion. In this case, broadband light as white color light from white color LED 23 enters the green color narrow band filter 71.

Then, only green color narrow band light is transmitted by the green color narrow band filter 71 and enters the rear end face of the light guide 27, and the guided narrow band light is emitted from the distal end face thereof.

The remaining part of the configuration is similar to that of the second embodiment.

The present variation has effects substantially similar to those of the above-described second embodiment.

Here, in the case of the present variation, if the light amount ratio between blue color narrow band light and green color narrow band light is adjusted to be constant as described with reference to FIG. 16, the light amount ratio may be adjusted to the following values. For example, if the adjustment is made using the area ratio, the above-described area ratio Sbi:Sgi may be adjusted to 4:1, and if the adjustment is made using the peak ratio, the above-described peak value ratio Pbi:Pgi may be adjusted to 6:1.

Next, a third variation of the second embodiment of the present invention will be described. For simplicity, the following description is provided in terms of a case where in a WLI mode, only a white color LED 23 is turned on and in an NBI mode, a blue color LED 25 and a green color LED 63 are turned on.

While in the related art examples, a blind state (a state in which no observed image is provided) occurs for a moment when an imaging mode is switched to another, in the present variation, imaging can be performed without occurrence of such blind state. Thus, when an imaging mode is switched to another, the timing is controlled so that simultaneous lighting (light emission) lasts for a predetermined period. The timing control described below is performed by a control circuit 34 provided in, for example, the endoscope 2B' but can be performed by a control circuit 34 provided in a processor 3.

Figure 19A:
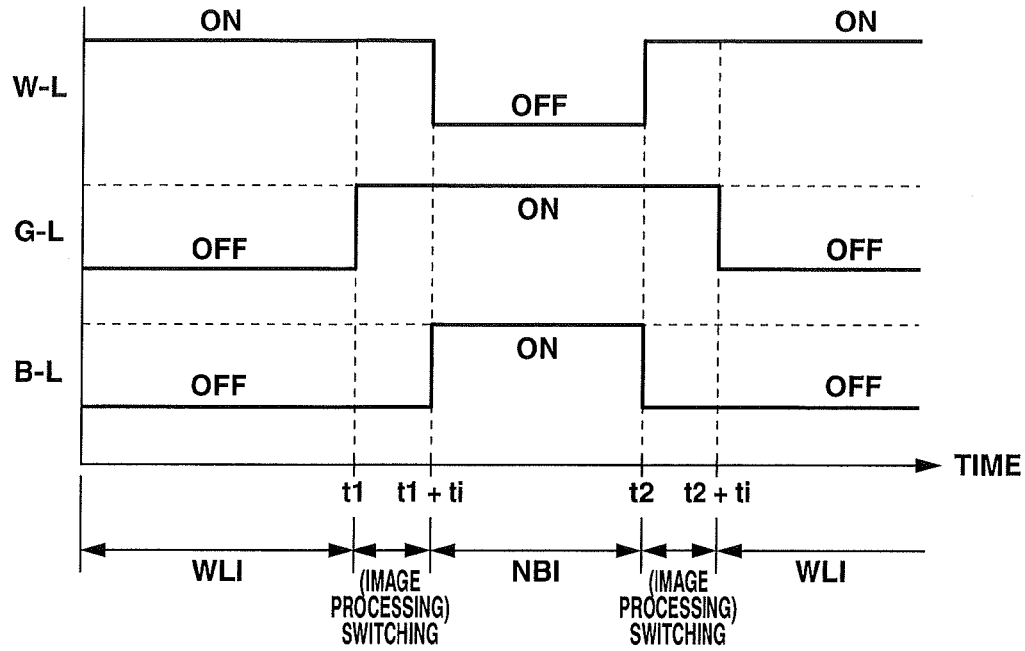
FIG. 19A is a timing chart illustrating operation control performed by a control circuit according to switching of imaging modes in a third variation of the second embodiment.

FIG. 19A is a diagram illustrating an operation when an operation to switch the WLI mode to the NBI mode is performed at a timing of a time t1, and an operation to switch the NBI mode to the WLI mode is performed at a timing of a time t2.

Before the time t1, only the white color LED 23 is on under the control of the control circuit 34, and in the switching operation at the time t1, the control circuit 34 turns the green color LED 63 on, and time ti for image processing switching from the time t1, turns the blue color LED 23 on and turns the white color LED 23 off. In the drawings in FIG. 19A onwards, for simplicity, the white color LED, the green color LED and the blue color LED are abbreviated as W-L, G-L and B-L, respectively.

During the time t1 for image processing switching, an image resulting from lighting of the white color LED 23 and an image resulting from lighting of the green color LED 63 are combined and displayed on the monitor 4.

Accordingly, even if the switching operation is performed at the time t1, the image resulting from lighting of the white color LED 23 and the image resulting from lighting of the green color LED 63 are combined and displayed on the monitor 4, and thus, no blind state occurs.

At a timing of a time t2, the control circuit 34 turns the white color LED 23 on and turns the blue color LED 23 off, and furthermore, after elapse of the time t1 requiring image processing switching, turns the green color LED 63 off from an on state.

Accordingly, when a switching operation is performed at the time t2, also, no blind state occurs as in the case of the time t1.

According to the present variation, an observed image without occurrence of a blind state even during switching can be obtained, enabling solution of problems of, for example, losing a region to be observed on which attention has been focused for a moment.

Figure 19B:
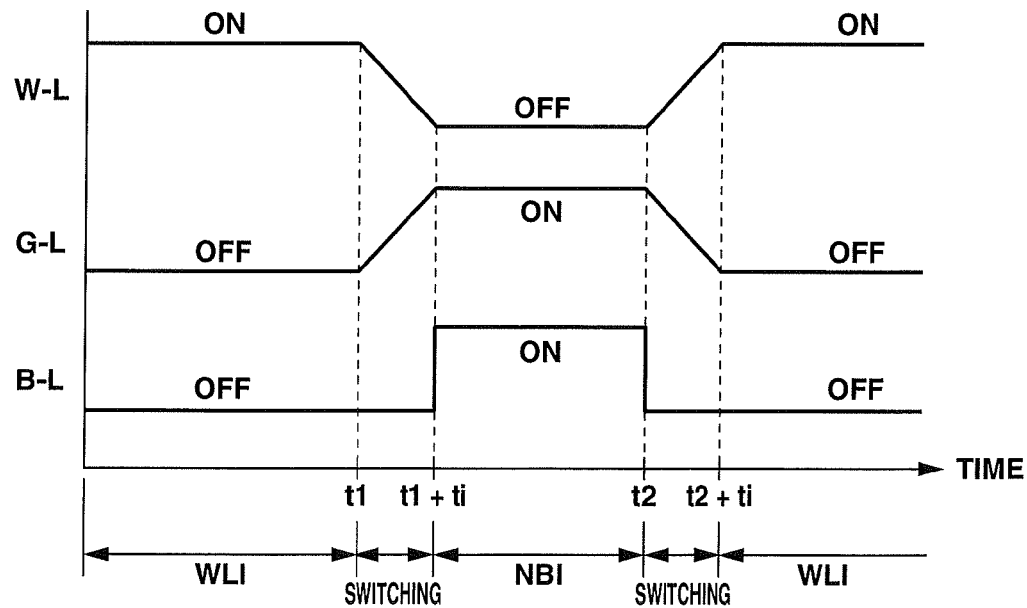
FIG. 19B is a timing chart illustrating operation control performed by the control circuit in the third variation in FIG. 19A.

As a variation of the control method illustrated in FIG. 19A, the control illustrated in FIG. 19B may be performed.

In FIG. 19B, when a switching operation is performed at a timing that is the same as in FIG. 19A, during time ti for image processing switching, the white color LED 23 and the green color LED 63 are made to transition from on to off by gradually decreasing the current or from off to on by gradually increasing the current.

Figure 19C:
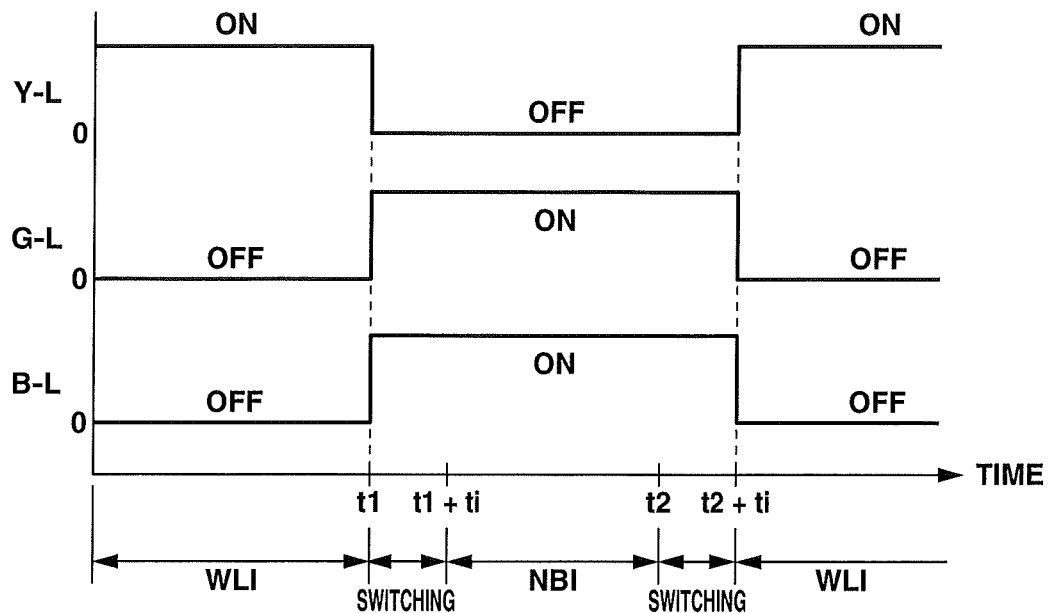
FIG. 19C is a timing chart illustrating operation control performed by a control circuit in another variation of FIG. 19A.
Figure 19D:
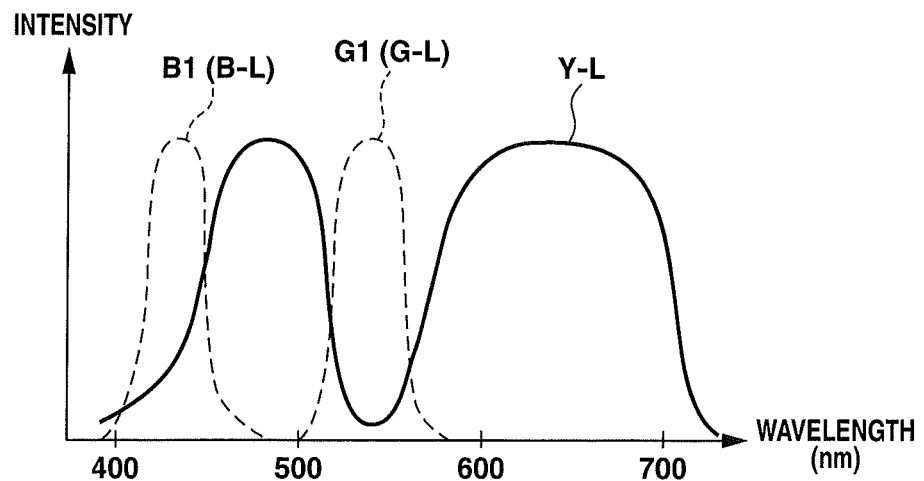
FIG. 19D is a diagram illustrating wavelength bands of broadband light, etc., generated by a yellow color LED, etc. in the case of FIG. 19C.

Furthermore, instead of the white color LED 23, as illustrated in FIG. 19D, a yellow color LED (abbreviated as Y-L in FIGS. 19C and 19D) that generates light in a yellow color wavelength band may be employed.

Then, if a switching operation is performed at a timing that is the same as that of FIG. 19A, the control circuit 34 may perform the control as illustrated in FIG. 19C.

As illustrated in FIG. 19C, when the yellow color LED, the blue color LED 25 and the green color LED 63 emit light, a characteristic close to that of white color light is provided. Accordingly, where the yellow color LED is used, on/off of the yellow color LED is controlled as illustrated in FIG. 19C.

Figure 20:
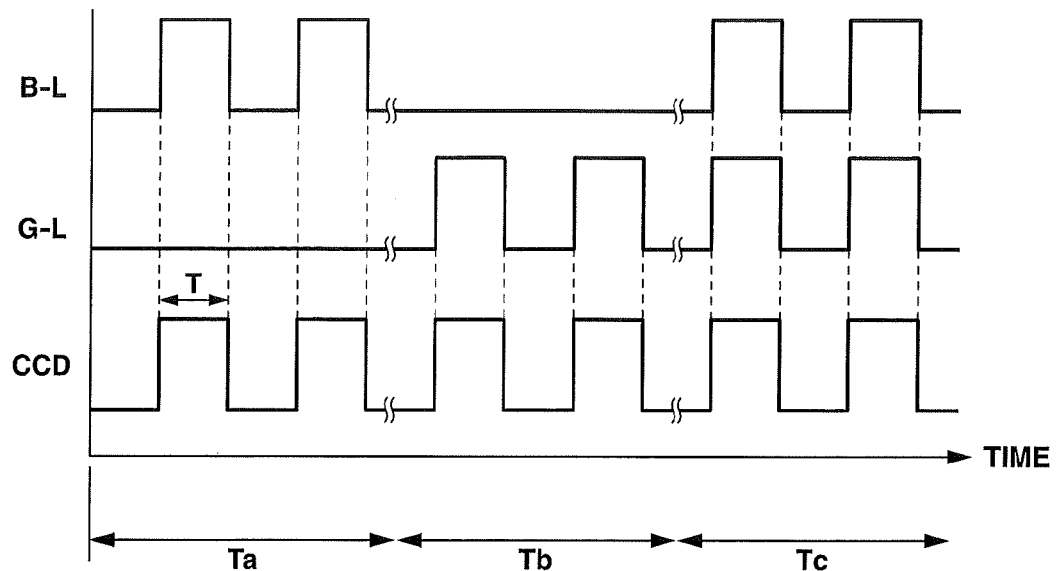
FIG. 20 is an operation illustration diagram illustrating drive operations of light emitting sections and an image pickup device in an NBI mode.

In an NBI mode, as illustrated in FIG. 20, control may be performed so that corresponding LED(s) are lighted (made to emit light) only in exposure periods of the CCD 17, which is an image pickup device.

FIG. 20 illustrates a case where the green color LED 63 and the blue color LED 25 can emit light in the NBI mode, and the control circuit 34 makes only one of the green color LED 63 and the blue color LED 25 emit light or both of the green color LED 63 and the blue color LED 25 emit light simultaneously in exposure period or image periods T (periods in which light is received and charge is accumulated) in which the CCD 17 actually pick up images according to a surgeon's selection.

In a period Ta in FIG. 20, an NBI mode using the blue color LED 25 is selected by a surgeon, in a period Tb, an NBI mode using the green color LED 63 is selected by the surgeon, and in a period Tc, an NBI mode using the blue color LED 25 and the green color LED 63 is selected by the surgeon.

Figure 21A:
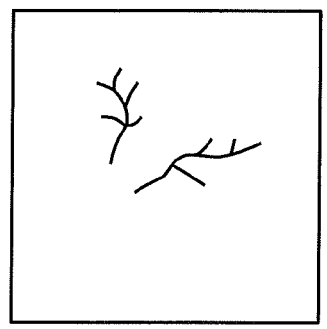
FIG. 21A is a schematic diagram of an NBI image obtained when a blue color LED emits light.
Figure 21B:
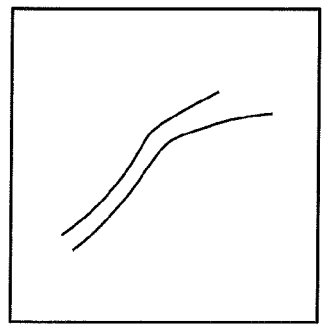
FIG. 21B is a schematic diagram of an NBI image obtained when a green color LED emits light.
Figure 21C:
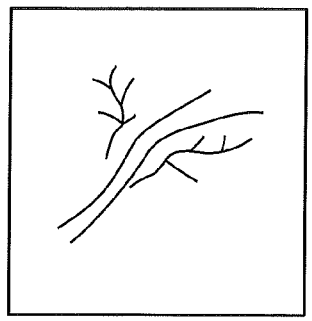
FIG. 21C is a schematic diagram of an NBI image obtained when a blue color LED and a green color LED emit light.

In the period Ta, an NBI image is an image in which flow in capillary vessels in a vicinity of a superficial layer can clearly and easily recognized as illustrated in FIG. 21A, in the period Tb, an NBI image in which flow in thick vessels in a part somewhat on the deep layer side relative to the superficial layer can clearly and easily be recognized is provided as illustrated in FIG. 21B. Furthermore, in the period Tc, an NBI image is one in which flow in vessels in the vicinity of the superficial layer and in the vicinity of a part with a depth somewhat on the deep layer side relative to the superficial layer as illustrated in FIG. 21C (like a combination of FIGS. 21A and 21B) can clearly and easily be recognized.

Also, control can be performed as in the period Tc to select display in FIG. 21A or FIG. 21B according to selection of a display mode for the monitor 4; however, the illumination on the non-selected side is wasted.

Although FIG. 20 illustrates a control method in NBI mode has been described, such control method can be applied to WLI mode cases.

As a result of the control as illustrated in FIG. 20, light emission can be prevented during periods in which the CCD 17 does not pick up images, enabling power saving. Furthermore, heat generated by the distal end portion 11 can be reduced.

Figure 22A:
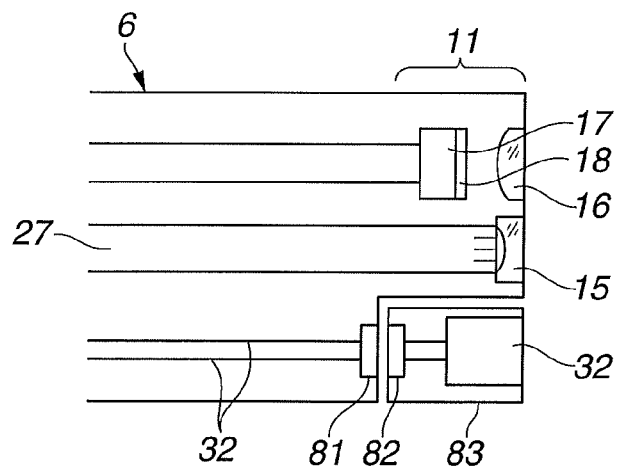
FIG. 22A is a diagram illustrating an example configuration in which a second light source section is detachably provided in a distal end portion of an insertion portion.

In the case of, for example, a configuration such as illustrated in FIG. 12, a second light source section may detachably be provided in a distal end portion 11 as illustrated in FIG. 22A. In FIG. 22A, for example, a cutout portion is formed in a distal end portion 11, and a connector receiver 81 is provided at an end face of the cutout portion. Then, a block 83 that includes the second light source section 22 illustrated in FIG. 12 and is provided with a connector 82 that is attachable/detachable to the connector receiver 81 is detachably attached to the cutout portion. The block 83 is set to have an outer shape fitting the cutout portion. Here, a power supply wire 32 is connected to the second light source section 22 via the connector receiver 81 and the connector 82.

Although the block 83 illustrated in FIG. 22A is one including a light source section for NBI, a block including a light source section for fluorescence imaging may be provided to use such block as a replacement.

Furthermore, for fluorescence imaging, there is a diagnosis method called PDD (photo dynamic diagnosis) in which a photosensitive substance having affinity for tumor is absorbed in a tumor part in advance and excitation light is applied to the tumor to make the tumor produce fluorescence, whereby the tumor is examined, and a block including a light source section that generates excitation light in such case may be provided.

In the case of the configuration in FIG. 22A, a surgeon can perform, e.g., NBI or fluorescence imaging by attaching a block that the surgeon wishes to actually use from among ones for NBI and fluorescence imaging, etc.

Figure 22B:
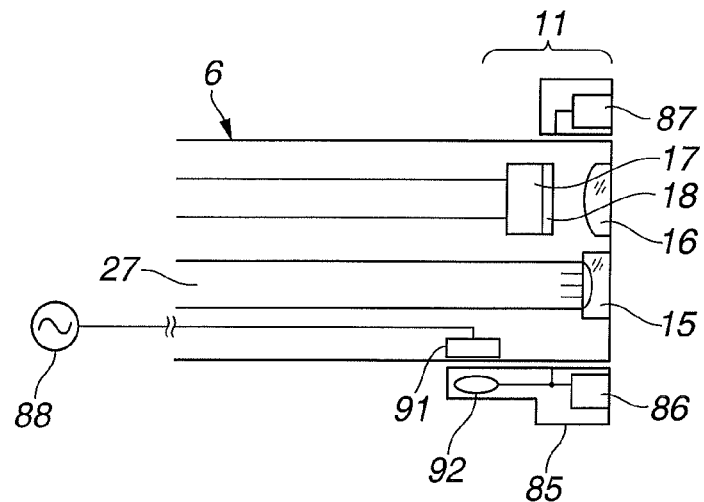
FIG. 22B is a diagram illustrating an example configuration of a variation of FIG. 22A.

Furthermore, as illustrated in FIG. 22B, it is also possible that a light source unit for NBI (hereinafter abbreviated as "light source unit") 85 is detachably attached to a distal end portion 11 of an endoscope including no second light source section.

In the configuration illustrated in FIG. 22B, the light source unit 85 has a ring shape having an inner diameter fitting an outer circumferential face of the distal end portion 11, and includes a B light source section 86 and a G light source section 87 that generate blue color narrow band light and green color narrow band light, respectively.

Also, in the endoscope, alternate-current power from an alternate-current power supply 88 is transmitted via a transmission wire and supplied to a power feeding section 91 provided in the distal end portion 11.

Furthermore, the light source unit 85 includes a power feeding receiving section 92 disposed at a position opposed to the power feeding section 91, the power feeding receiving section 92 receiving alternate-current power (with no contacts, that is) in a contactless manner, and the power feeding receiving section 92 converts the alternate-current power into a direct-current power by means of a rectifier circuit provided inside thereof to supply drive power to the B light source section 86 and the G light source section 87. The endoscope provides an effect of enabling NBI by attaching the light source unit 85 thereto.

Embodiments configured by partially combining the above-described embodiments, etc., also belong to the present invention.

In the above-described embodiments or the variations thereof, those using, for example, a half mirror that transmits and reflects white color light and blue color light or green color light at a predetermined ratio and guides the light to the emission face side instead of using the dichroic prism formed by the prism 28 or 61 also belongs to the present invention.

What is claimed is:

1. An endoscope comprising:
an insertion portion to be inserted into a subject;
an operation portion provided at a proximal end of the insertion portion, the operation portion including operation means;
a first light source section provided inside the operation portion, the first light source section being configured to generate first light with which the subject is irradiated;
a light guiding section including an entrance portion provided on a proximal end side of the insertion portion and an emitting portion provided in a distal end portion of the insertion portion, the light guiding section being configured to attenuate light in a narrow wavelength band which is within a range of wavelength band of the first light entering the entrance portion and which is narrower than the wavelength band of the first light, and to emit the light from the emitting portion;
a second light source section provided at the distal end portion of the insertion portion, the second light source being configured to generate the light in the narrow wavelength band within the range of wavelength band of the first light, the light being attenuated by the light guiding section, as second light; and
an optical element provided at the distal end portion of the insertion portion, the optical element combining light emitted from the emitting portion of the light guiding section and the second light and emitting the resulting light from an illuminating window provided at the distal end portion.

2. The endoscope according to claim 1,
wherein the first light source section includes a white color light-emitting diode that substantially generates white color light covering a visible wavelength band, as the first light;
wherein the wavelength band in which attenuation occurs when the first light is guided by the light guiding section includes a blue color narrow band; and
wherein the second light source section includes a blue color light-emitting diode that generates light in the blue color narrow band, as the second light.

3. The endoscope according to claim 2, wherein the first light source section further includes a green color light-emitting diode that generates green color narrow band light, and the endoscope further includes a light amount adjusting section configured to adjust a light amount ratio between an amount of the blue color narrow band light emitted via the optical element and an amount of the green color narrow band light from the green color light-emitting diode, the green color narrow band light being emitted via the optical element.

4. The endoscope according to claim 2, wherein the optical element selectively combines light in a wavelength band other than the wavelength band in which attenuation occurs when the first light is guided by the light guiding section in the light emitted from the emitting portion of the light guiding section, with the second light.

5. The endoscope according to claim 4, further comprising an imaging mode selecting section configured to make a selection of one of a first light imaging mode in which first light imaging using illumination with the first light is performed and a second light imaging mode in which second light imaging using illumination with the second light is performed, and a control section configured to control light emission operations of the first light source section and the second light source section based on the selection made by the imaging mode selecting section.

6. The endoscope according to claim 5, wherein the control section, upon selection of the first light imaging mode, performs control so as to make the first light source section and the second light source section emit light simultaneously, and upon selection of the second light imaging mode, performs control so as to make the first light source section not emit light and selectively make only the second light source section emit light.

7. The endoscope according to claim 6, further comprising a first light/second light imaging mode selecting section configured to make a selection of a first light/second light imaging mode in which first light illumination with the first light and second light illumination with the second light are alternately provided to acquire a first light image using the first light illumination and a second light image using the second light illumination,
wherein based on the selection made by the first light/second light imaging mode selecting section, the control section controls light emission operations of the first light source section and the second light source section.

8. The endoscope according to claim 7, wherein in a first light illumination period in which the first light illumination is provided, the control section performs control so as to make the first light source section and the second light source section emit light simultaneously, and in a second light illumination period in which the second light illumination is provided, the control section performs control so as to make the first light source section not emit light and selectively make only the second light source section emit light.

9. The endoscope according to claim 8, wherein in the second light illumination period, the control section controls a light emission operation of the blue color light-emitting diode included in the second light source section so that a light emission amount is increased relative to that in the first light illumination period.

10. The endoscope according to claim 8, further comprising an image pickup device disposed in a distal end portion of the insertion portion, the image pickup device picking up an image of an object under the first light illumination and the second light illumination,
wherein the control section controls a signal processing circuit provided in an outside apparatus to which the endoscope is connected, the signal processing circuit performing signal processing for the image pickup device, to:
generate the first light image from a signal picked up by the image pickup device in the first light illumination; and
generate the second light image from a signal picked up by the image pickup device in the second light illumination.

11. The endoscope according to claim 10, wherein the control section further controls the signal processing circuit to generate a composite image in which the first light image and the second light image are simultaneously displayed adjacent to each other.

12. The endoscope according to claim 9, further comprising a period setting section configured to set a value of each of a period of the first light illumination and a period of the second light illumination, which are alternately provided.

13. The endoscope according to claim 4,
wherein the first light source section includes:
the white color light-emitting diode;
a green color light-emitting diode that generates green color narrow band light;
a second optical element including a first entrance face and a second entrance face that white color light from the white color light-emitting diode and green color narrow band light from the green color light-emitting diode enter, respectively,
the second optical element selectively allowing light other than light having a wavelength band of the green color narrow band light in the white color light entering from the first entrance face to enter the entrance portion of the light guiding section, and
the second optical element selectively allowing light having a wavelength band of the green color narrow band light in the green color narrow band light entering from the second entrance face to enter the entrance portion of the light guiding section.

14. The endoscope according to claim 2, further comprising a light source fixing portion configured to fix the first light source section and the entrance portion of the light guiding section in contact with each other.

15. The endoscope according to claim 2, further comprising a timing control section configured to perform timing control so that when light irradiation by the first light source section and light irradiation by the second light source section are switched from one to another, the first light source section and the second light source section are lighted simultaneously for a predetermined period.

16. The endoscope according to claim 2, wherein a polarizer is disposed between the second light source section and the optical element.

17. The endoscope according to claim 1, wherein the second light includes light for producing the first light as a result of the light being combined with light emitted from the emitting portion of the light guiding section by the optical element.

18. The endoscope according to claim 1, further comprising:
a cable extending from the operation portion; and
a power supply wire inserted in the cable, wherein the first light source section receives a supply of drive power for making the first light source section emit light, from a power supply circuit disposed outside the endoscope via the power supply wire.

19. The endoscope according to claim 1, wherein the operation portion is integrally formed at the proximal end of the insertion portion, and includes a bending operation knob for bending and operating a bending portion provided in the insertion portion, as the operation means.

20. The endoscope according to claim 1, wherein the optical element comprises a dichroic prism that selectively reflects the second light entered from the second light source section and selectively transmits light in a broadband wavelength other than a wavelength band of the second light in the first light entered from the first light source section.

21. The endoscope according to claim 1, wherein
the first light source section comprises a white color light emitting diode that emits white color light including light in red, green, and blue wavelength bands in the operation portion, and
the light guiding section comprises a light guide that transmits the white color light.

22. The endoscope according to claim 1, wherein the first light source section generates light including a visible wavelength band as the first light, and the light guiding section attenuates light in a wavelength band which is within the visible wavelength band and narrower than the visible wavelength band of the first light.

* * * * *